US005849876A

United States Patent [19]
Linsley et al.

[11] Patent Number: 5,849,876
[45] Date of Patent: Dec. 15, 1998

[54] HYBRIDOMAS PRODUCING MONOCLONAL ANTIBODIES TO NEW MUCIN EPITOPES

[75] Inventors: Peter S. Linsley; Diane Horn; Joseph P. Brown, all of Seattle, Wash.

[73] Assignee: Sanofi, Paris, France

[21] Appl. No.: 179,875

[22] Filed: Jan. 11, 1994

Related U.S. Application Data

[63] Continuation of Ser. No. 913,740, Jul. 14, 1992, abandoned, which is a continuation of Ser. No. 104,511, Oct. 8, 1987, abandoned, which is a continuation-in-part of Ser. No. 932,781, Nov. 19, 1986, abandoned.

[51] Int. Cl.$^6$ .................. A61K 39/395; C07K 16/00
[52] U.S. Cl. .................... 530/387.7; 424/155.1; 424/156.1; 424/157.1; 424/174.1; 435/70.21; 435/172.2; 530/388.8; 530/388.85; 530/389.7; 530/391.3; 530/391.7
[58] Field of Search .................. 424/85.8, 85.91, 424/155.1, 156.1, 157.1, 174.1; 435/70.21, 172.2, 240.27; 530/387.7, 388.8, 388.85, 389.7, 391.3, 391.7

[56] References Cited

U.S. PATENT DOCUMENTS

| | | | |
|---|---|---|---|
| 4,485,093 | 11/1984 | Runge et al. | 530/391 |
| 4,522,918 | 6/1985 | Schlom et al. | 435/68 |
| 4,584,268 | 4/1986 | Ceriani et al. | 436/542 |
| 4,612,282 | 9/1986 | Schlom et al. | 435/68 |
| 4,628,032 | 12/1986 | White et al. | 530/387 |
| 4,643,971 | 2/1987 | Fradet et al. | 530/387 |
| 4,650,756 | 3/1987 | Old et al. | 435/68 |
| 4,678,747 | 7/1987 | Lloyd et al. | 435/7 |
| 4,683,200 | 7/1987 | Hirohashi et al. | 435/68 |
| 4,707,438 | 11/1987 | Keydar et al. | 435/5 |
| 4,731,238 | 3/1988 | Neville et al. | 424/85.8 |
| 4,752,569 | 6/1988 | Terasaki et al. | 435/7 |
| 4,753,894 | 6/1988 | Frankel et al. | 436/548 |
| 4,803,169 | 2/1989 | Linsley et al. | 435/7 |
| 4,814,275 | 3/1989 | Durda et al. | 530/387 |
| 4,818,682 | 4/1989 | Linnane | 435/7 |
| 4,863,854 | 9/1989 | Mattes et al. | 530/387 |
| 4,916,213 | 4/1990 | Scannon et al. | 424/85.8 |
| 4,935,344 | 6/1990 | Bander et al. | 435/7 |
| 4,938,948 | 7/1990 | Ring et al. | 424/9 |
| 4,960,716 | 10/1990 | Harvey et al. | 436/542 |

FOREIGN PATENT DOCUMENTS

| | | |
|---|---|---|
| 0118365 | 12/1984 | European Pat. Off. . |
| 0160446 | 6/1985 | European Pat. Off. . |
| 0161941 | 11/1985 | European Pat. Off. . |
| 0174534 | 3/1986 | European Pat. Off. . |
| 0184369 | 6/1986 | European Pat. Off. . |
| 0184370 | 6/1986 | European Pat. Off. . |
| 86303042 | 11/1986 | European Pat. Off. . |
| 86110709 | 3/1987 | European Pat. Off. . |
| 86307735 | 5/1987 | European Pat. Off. . |
| 87301040 | 8/1987 | European Pat. Off. . |
| 2131830 | 6/1984 | United Kingdom . |
| WO8502411 | 6/1985 | WIPO . |
| 8600414 | 1/1986 | WIPO . |
| 8602735 | 5/1986 | WIPO . |

OTHER PUBLICATIONS

Swallow, D.M., Griffiths, B., Bramwell, M., Wiseman, G., and Burchell, J. (1986) Detection of the Urinary 'PUM' Polymorphism by the Tumour–Binding Monoclonal Antibodies Ca1, Ca2, Ca3, HMFG1, and HMFG2. Disease Markers. 4:247–254 (Exhibit 2).

Papsidero, L.D., Croghan, G.A., Johnson, E.A., and Chu, T.M. (1984) Immunoaffinity Isolation of Ductal Carcinoma Antigen Using Monoclonal Antibody F36/22. Molecular Immunology. 21(10):955–960 (Exhibit 3).

Johnson, V.G., Schlom, J., Paterson, A.J., Bennett, J.,Magnani, J.L., and Colcher, D. (1986) Analysis of a Human Tumor–associated Glycoprotein (TAG–72) Identified by Monoclonal Antibody B72.3. Cancer Research. 46:850–857 (Exhibit 4).

Frankel et al., *J. Biol. Resp. Mod.* 4:273–286, Jun. 1985.

Miotti et al., "Biochemical analysis of human ovarian cancer–associated antigens defined by murine monoclonal antibodies", Chem. Abstr. 102(13) (1985) (Abstr. No. 11057t).

Mattes et al., "Three mouse monoclonal antibodies to human differentiation antigens: reactivity with two mucin–like antigens and with connective tissue fibers" *Chem. Abstr.*, 103 (1985) (Abstr. No. 212955k).

Linsley et al., "Heritable variation in expression of multiple tumor associated epitopes on a high molecular weight mucin–like antigen", Chem. Abstr., 106(5) (1987) (Abstr. No. 31057k).

Swallow et al., "Detection of the urinary 'PUM' polymorphism by the tumor–binding monoclonal antibodies Ca1, Ca2, Ca3, HMFG1 and HMFG2", *Chem. Abstr.* 106(19) (1987) (Abstr. No. 154350h).

Linsley et al., "Monoclonal antibodies reactive with mucin glycoproteins found in sera from breast cancer patients", *Chem. Abstr.* 108 (23) (1988) (Abstr. No. 202883z).

Linsley et al., "Elevated Levels of a High Molecular Weight Antigen Detected by Antibody W1 in Sera from Breast Cancer Patients", *Cancer Research* 46:5444–5450 (1986).

Burchell et al., "Complexity of Expression of Antigenic Determinants, Recognized by Monoclonal Antibodies HMFG–1 and HMFG–2, in Normal and Malignant Human Mammary Epithelial Cells", *J. Immunol.*, 131:508–513 (1983).

(List continued on next page.)

*Primary Examiner*—Laurie Scheiner
*Attorney, Agent, or Firm*—Merchant, Gould, Smith, Edell, Welter & Schmidt

[57] ABSTRACT

Novel hybridoma cell lines producing monoclonal antibodies reactive with purified mucin antigens from normal and tumor sources are generated using mucins, including purified mucins from tumor sources. Epitopes on mucin antigens from normal and tumor sources are demonstrated to be distinct, using these new antibodies. The antibodies may be useful alone or in combination, in the diagnosis and treatment of cancer including malignancies of the breast and lung.

3 Claims, 5 Drawing Sheets

OTHER PUBLICATIONS

Sekine et al., "Purification and Characterization of a High Molecular Weight Glycoprotein Detectable in Human Milk and Breast Carcinomas", J. Immunol., 135: 3610–3615 (1985).

Kufe et al., "Differential Reactivity of a Novel Monoclonal Antibody (DF3) with Human Malignant versus Benign Breast Tumors", *Hybridoma* 3:223–231 (1984).

Frankel et al., "Tissue Distribution of Breast Cancer–Associated Antigens Defined by Monoclonal Antibodies", *J. Biol. Resp. Modifiers* 4:273–286 (1985).

Springer and Desai, "Tn Epitopes, Immunoreactive with Ordinary Anti–Tn Antibodies, on Normal, Desialyted Human Erythrocytes and on Thomsen–Friedenreich Antigen Isolated Therefrom", *Molecular Immunology*, 22:1303–1310 (1985).

Nakani and Kawoi, "Peroxidase–Labeled Antibody, a New Method of Conjugation" Journal of Histochem and Cytochem., 22:1084–1091 (1974).

Springer, "T and Tn, General Carcinoma Autoantigens", *Science* 224:1198–1206 (1984).

Creeth et al., "The Separation and Characterization of Bronchial Glycoproteins by Density–Gradient Methods" *Biochem. J.*. 167:557–569 (1977).

Linsley et al., "Identification of a Novel Serum Protein Secreted by Lung Carcinoma Cells", *Biochemistry* 25:2978–2985 (1986).

Johnson et al., "Analysis of a Human Tumor–associated Glycoprotein (TAG–72) identified by Monoclonal Antibody B72.3", Cancer Res., 46:850857 (1986).

Hilkens et al., "MAM–6 Antigen, A New Serum for Breast Cancer Monitoring" Cancer Res., 46:2582–2587 (1986).

Hilkens et al., "MAM–6, a Carcinoma Associated Marker: Preliminary Characterisation and Detection in Sera of Breast Cancer Patients" in Monoclonal Antibodies and Breast Cancer, Cercani, Ed., pp. 28–42, The Hague, Martinus, Nijhoff (1985).

Brown et al., "Quantitative Analysis of Melanoma–Associated Antigen p97 in Normal and Neoplastic Tissues", Proc. Natl. Acad. Sci. USA, 78(1):539–543 (1981).

Taylor–Papadimitriou & Gendler, "Molecular Aspects of Mucins", *Cancer Res. Rev.* 11:11–24 (1988).

Linsley et al., "Monoclonal Antibodies Reactive with Mucin Glycoproteins Found in Sera from Breast Cancer Patients", *Cancer Res.*, 48–2138–2148 (1988).

Linsley et al, Cancer Res., 46, 5444–50, (Oct. 1986).

Papsidero et al, Cancer Res., 44, 4653–7, (Oct. 1984).

Frankel et al, J Biol Resp Mod., 4, 273–86, (Jun. 1985).

Bara et al, Cancer Res., 43, 3885–91 (Aug. 1983).

Gold et al, J. Biol. Chem, 256(12), 6354–8, (1981).

Campbell, Monoclonal Antibody Technology, Chapters 3, 4, 6, to 10, (Elsevier), 1985.

Waldmann, T.A., "Monoclonal Antibodies in Diagnosis and Therapy," *Science* vol. 252:1657–1662, 21 Jun. 1991.

Papsidero et al., Mol. Immunol., 21(10), 955–60, (1984).

Ceriani et al, Som. Cell. Gen., 9(4), 415–27 (1983).

Burchell et al., MAb to Breast Cancer and Their Application, in Monoclonal Antibodies for Cancer Detection and Therapy (Baldwin et al., Eds), pp. 1–15 (1985).

Price et al., Br J Cancer, 54, 393–400 (1986).

Gangopadhyay et al., "Immunoperoxidase localization of a high molecular weight mucin recognized by monoclonal antibody ID3", *Chem. Abstr.* 102(21) (1985) (Abstr. No. 183526t).

Papsidero et al., "Immunoaffnity isolation of ductal carcinoma antigen using monoclonal antibody F36/22", *Chem. Abstr.*, 102(1) (1985) (Abst. No. 4265u).

Watanabe et al., "Carbohydrate antigen defined by a monoclonal antibody raised against a gastric cancer xenograft", Chem. Abstr., 102(19) (1985) (Abstr. No. 164975x).

HYBRIDOMAS PRODUCING MONOCLONAL ANTIBODIES TO NEW MUCIN EPITOPES

CROSS REFERENCE TO RELATED APPLICATION

This application is a file wrapper continuation application of U.S. Ser. No. 07/913,740, filed Jul. 14, 1992, now abandoned which is a file wrapper continuation of U.S. Ser. No. 07/104,511, filed Oct. 8, 1987, now abandoned, which is a continuation-in-part of U.S. patent application Ser. No. 932,781, filed Nov. 19, 1986, now abandoned.

FIELD OF THE INVENTION

This invention relates to hybridoma cell lines that produce new monoclonal antibodies reactive with mucins, particularly to purified mucins, and more particularly to monoclonal antibodies that are capable of preferentially recognizing new epitopes on mucins associated with malignant tissue, useful for the detection and treatment of human cancers, particularly breast cancer.

BACKGROUND OF THE INVENTION

Mucins are heavily glycosylated, high molecular weight glycoproteins with a carbohydrate content of up to 80% that are secreted by seroviscous tissues in the mouth, lungs, cervix and intestines. Mucins have been identified as tumor-associated antigens and have been isolated from the serum and ascites fluid of cancer patients, including those with breast cancer.

The fat globules of human milk are contained in a particular membrane derived from the plasma membrane of the apical surfaces of lactating cells. Interest in this membrane, known as the milk fat globule membrane (hereafter MFGM), has increased with the demonstration that some of the antigens found within the MFGM are mucin-like and are tumor-associated, particularly with carcinomas of the breast. Antibodies directed to epitopes on mucin antigens associated with breast cancer have been obtained from mice immunized with fragments of human milk fat globule (HMFG). These antibodies show promise for the diagnosis of breast tumors. Of particular interest are antibodies directed against high molecular weight (Mr greater than 200,000) mucin-like components of the MFGM. Antibodies to mucin-like antigens have been used successfully to diagnose micro-metastases in biopsies, as an indicator of tumor prognosis for radio-localization of tumors, and for serum assays to monitor tumor progression. Linsley et al., *Cancer Research*, 46, p. 5444–5450, (1986), incorporated by reference herein.

Most of the mucin antigens previously characterized have been found to be present in normal tissues in addition to tumor tissue. Variations in mucin-like antigens from normal and tumor sources have been studied by Burchell et al., *J. Immunol.*, 131, p. 508 (1983), who found differences in the ratios of determinants recognized by two monoclonal antibodies (HMFG-1) and (HMFG-2) in normal human breast epithelial cells and in breast tumor cell lines. These investigators showed that the relative levels of binding of HMFG-1 and HMFG-2 varied between cell lines from normal and malignant breast epithelium, with the HMFG-2 epitope being more strongly expressed on the tumor cell lines. Sekine et al., in *J. Immunol.*, 135, p. 3610 (1985), compared mucin-like antigens reactive with the DF3 monoclonal antibody, Kufe et al., *Hybridoma*, 3, p. 223 (1984), from milk and pleural effusion fluids from breast cancer patients. These studies suggest that mucins are antigenically complex, expressing a variety of epitopes on both normal and tumor tissues, and also indicate that mucins may vary in the expression of epitopes between different tissue sources. Antibodies that react with epitopes on mucin-like antigens that are found at elevated levels in sera from breast cancer patients, have also been described (Linsley et al., supra, and Frankel et al., *J. Biol. Response Modifiers*, 4, p. 273 (1985)). One of these antibodies, W1, is reactive with epitopes on a mucin antigen associated with breast cancer cells. W1 antibody has been used in an assay to detect the presence of antigen at elevated levels in serum from breast cancer patients (Linsley et al., supra). In addition to the W1 epitope, other epitopes, such as the T (Thomsen-Friedenreich) and Tn mucin epitopes which have been known to be associated with carcinomas, may be detected in an assay using monoclonal antibodies. Springer and Desai, *Molecular Immunology*, 22, pp. 1303–1310 (1985); and Springer, *Science* 224, pp. 1198–1206 (1984).

It would be desirable to develop new antibodies which demonstrate increased specificity in assays for tumor-associated antigens present in samples from human subjects. Optimally, such antibodies should be capable of identifying specific epitopes on a tumor-associated mucin antigen, which epitopes are found at greatly reduced levels on, or are masked on antigen derived from normal tissues. Such antibodies could then be used to perform more sensitive assays for detecting the presence of cancer by preferentially reacting with tumor-associated antigens in sera from patients with cancer.

SUMMARY OF THE INVENTION

Accordingly, the present invention provides new hybridoma cell lines that produce monoclonal antibodies to mucin antigens purified from normal (non-tumor) or tumor tissue sources. Certain of the hybridomas are generated using protocols which include purified mucin antigen as the immunogen. The monoclonal antibodies of this invention may be used to perform serum assays to detect the presence of tumor-associated mucin antigens. In addition, assays to detect mucin antigens in biological specimens, including sputum and bronchial brushings and lavage specimens, may be performed using these antibodies. As such, the antibodies produced by the hybridoma cell lines of this invention may promote the diagnosis and treatment of human cancer, including breast and lung malignancies.

At least one of the new monoclonal antibodies produced using purified tumor mucin antigen, the monoclonal antibody Onc-M26, demonstrates a preferential recognition of tumor associated mucin antigen as compared to antigen derived from normal sources. The Onc-M26 antibody has substantially reduced reactivity with antigen isolated from normal sources. In addition, monoclonal antibody M38 exhibits high specificity to a unique epitope on mucin antigens.

Fourteen other new monoclonal antibodies as described herein, also react with tumor-associated mucin antigen. Additionally, these antibodies were reactive with antigens derived from normal individuals. Several of these new monoclonal antibodies appear to react with different epitopes on the W1 antigen than previously identified epitopes.

BRIEF DESCRIPTION OF THE DRAWINGS

The details of typical embodiments of the present invention will be described in connection with accompanying drawings in which.

DETAILED DESCRIPTION OF THE INVENTION

Figure 1:
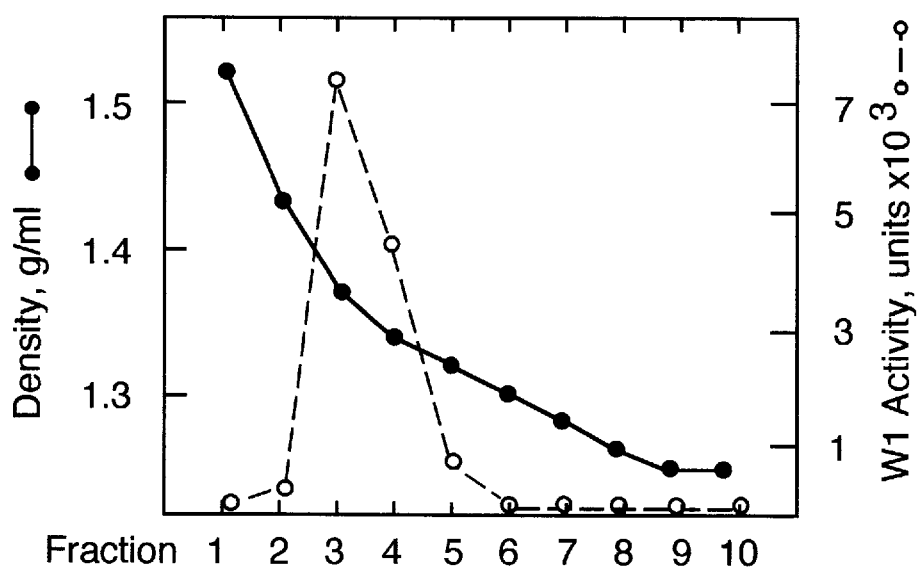
FIG. 1 depicts W1 antibody binding to fractions from a CsCl density gradient purification of milk mucins.

The hybridomas producing the monoclonal antibodies of the present invention are produced following the general procedures described by Kohler and Milstein, *Nature*, 256, p. 495 (1975), incorporated by reference herein. In that procedure, hybridomas are prepared by fusing antibody producing cells (typically spleen cells of mice previously immunized with a mucin antigen source) to cells from an immortal tumor cell line using somatic cell hybridization procedures. The agents used for immunization of animals ("immunogens") to induce production of antibodies to mucin antigens, have typically consisted of live human cancer cells, for example breast cancer cells, or MFGM, or cancer cell membrane extracts. Inoculations of more than one type of immunogen may be given, for example, cancer cells and MFGM may be introduced in separate immunizations. In addition to MFGM, and human cancer cell lines, the present invention makes use of purified mucins as immunogens including mucins obtained from tumor sources, as described below. Use of purified tumor-associated mucins as immunogen may improve the chances of generating antibodies to distinct tumor-associated epitopes.

The novel monoclonal antibodies described herein were generated by immunizing mice with cancer cell lines; MFGM preparation; or mucins purified from milk or from pleural effusions from cancer patients, as summarized in Table 3 below. For immunization with purified mucin, the animals are inoculated intraperitoneally and/or subcutaneously at least once with 100 units or more of immunogen. Inoculations of more than one type of immunogen may be given, for example, cancer cells and MFGM. The animals are then boosted two or more times with immunogen. Spleens are harvested from the animals several days after the last boost, and a spleen cell suspension is prepared for fusion using known fusion techniques with murine myeloma cells.

The hybridomas resulting from the fusion process are allowed to grow. Thereafter, the resulting supernatants are screened using immunoassay procedures to detect antibodies present in the supernatants capable of binding to the specific antigens. In some cases, a lectin-capture assay (WGA), described below, was used as a preliminary screen to detect monoclonal antibodies present in supernatants capable of binding to purified milk and pleural effusion derived antigens, or capable of binding to mucin antigens in serum obtained from human subjects with and without cancer. In other cases, supernatants were screened for their ability to bind cultured cancer cells or MFGM. An enzyme immunoassay (ELISA) was used to detect binding of antibody to lectin-adhered purified mucin antigen, to cancer cells or to MFGM. Additional types of screening were performed on the hybridoma supernatants, including competition binding assays and observations of fluorescent binding patterns as described in the examples.

A double determinant immunoassay (DDIA) (Linsley et al., supra) which tests for antibody binding to epitopes on mucin antigen, such as the W1 epitope, was used to analyze the performance of the new monoclonal antibodies in human serum assays to detect tumor-associated mucin antigen and to compare the new antibodies with the W1 antibody, and in assays of bronchial brushings obtained during bronchoscopy of human subjects. The DDIA uses an antibody, preferably a monoclonal antibody ("capture" antibody) immobilized on a substrate, such as a plastic support or column, to capture antigen present in a fluid sample, such as blood serum, from a cancer patient. (Serum from a patient without cancer is used as a control.) A second antibody, also preferably a monoclonal antibody, is added which may be labeled for detection, for example, with a radionuclide such as Iodine-125 ($^{125}I$) or with Horseradish Peroxidase (HRP) (the "detecting" antibody). The labeled antibody will bind to any captured antigen to allow the detection and quantification of mucin antigen present in the sera. In some situations in which an antigen has repeating epitopes, such as the W1 epitope, the second antibody may be the same as the first antibody, for example, both being W1 antibody (homologous DDIA). For non-repeating epitopes it may be necessary to use a second antibody capable of binding to a different epitope on the antigen, for example, because an epitope is blocked by binding with the first antibody. The latter is referred to as a heterologous DDIA, and each assay is named according to the antibody used as the capture antibody, which is listed first, and the antibody used as a conjugate for detection. Thus the "M26/M29" assay uses M26 as the capture antibody and HRP-M29 as the detecting antibody conjugate.

Optimally, it is desirable to identify new epitopes on tumor-associated antigens to enable the production of monoclonal antibodies which are capable of performing an immunoassay with increased sensitivity and specificity, i.e., resulting in an assay that is better capable of distinguishing samples from persons having cancer from samples obtained from persons without cancer, and by reducing the occurrence of false positive results. False positive results occur when the assay indicates the presence of cancer where none is present in the patient, because antibody binds to epitopes on mucin antigen from normal sources. In addition, the sensitivity of an assay may be enhanced using antibodies with higher specificity for mucin antigens, particularly for epitopes on tumor-associated antigens; small amounts of antigen will be bound so that earlier stages of cancer in patients may be detected.

The following examples are presented to illustrate the present invention and to assist one of ordinary skill in making and using the same. The examples are not intended in any way to otherwise limit the scope of the disclosure or the protection granted by Letters Patent hereon.

EXAMPLE 1

Purification of Mucin Antigens from Tumor and Normal Sources

Sources of Mucin Antigen

Sources of mucin used in generating the monoclonal antibodies of the present invention were selected by testing a variety of samples obtained from milk, pleural effusion fluids and tumors from human subjects for antigenic activity. Antigenic activity was detected using a competitive cell binding assay, as described by Linsley et al., supra. This assay was also used to monitor mucin purification as described below. Briefly, in the selection procedure, samples were tested for their ability to inhibit the binding of $^{125}$I-labeled or HRP-conjugated W1 antibody to W5-6 cells. W5-6 is a cell line enriched in mucin antigens, and was derived from Calu-1 lung carcinoma cells as described below. One unit of inhibitory activity was defined as the amount of material causing a 50% reduction in binding of $^{125}$I-labeled or HRP-conjugated W1 antibody (added at a concentration of 0.4 μg/ml) to $3\times10^4$ W5-6 cells. Binding of $^{125}$I-labeled W1 antibody was detected by using a gamma counter, and bound HRP-conjugated W1 antibody was detected using an ELISA assay. The HRP was directly conjugated to the W1 antibody by a modification of the procedure of Nakani and Kawoi, *J. Histochem. Cytochem.*, 22, p. 1084 (1974). The conjugate had a molar HRP to antibody ratio of approximately 1:1. Bound HRP-WI antibody conjugates were detected by the addition of a solution of ortho-phenylenediamine (OPD) (100 μl) (Zymed Laboratories, Inc., San Francisco, Calif.) at a concentration of 0.5 μg/ml, in 100 mM sodium citrate at pH 5.0, containing 0.0075% (volume/volume) $H_2O_2$. A yellow color from the reaction of substrate with enzyme was allowed to develop until maximal absorbances of 0.4–1.5 (optical density units or O.D.) at 490 nm, as determined using a spectrophotometer, were reached. (These values are within the optimal range for the ELISA). The enzyme-substrate color reactions were terminated by the addition of 50 μl of 1.3N $H_2SO_4$, and absorbance at 490 nm was measured using a Microtiter® plate reader (Genetic Systems Corp., Seattle, Wash.). The W1 antibody was used because of its known reactivity with mucin antigens. Essentially identical values were obtained using either assay.

Following the above procedures, normal human milk which contains proteins derived from breast epithelium, as well as effusion fluids derived from cancer patients were found to contain high levels of W1 inhibitory activity (greater than 1000 units/ml). Because of the possibility of individual variations between samples not related to the malignant state, mucins were purified from four different milk samples and two pleural effusion samples. A pool of acid-ethanol extracted breast tumors from a large number of individuals was also used as a source for purification of mucins. The purification of mucins from these sources is described below.

Collection of Milk and Pleural Effusion Fluids

Milk was obtained from four cancer-free donors and designated as samples Milk 1, Milk 2, Milk 7, and Milk 11. The samples were frozen within 5 to 10 minutes after collection. Initially, both soluble and MFGM-associated forms of W1-binding mucins were found in the milk samples. To maximize the overall yield of mucin obtained, analysis was not restricted to the MFGM-associated form of the antigen from milk.

The effusions used contained predominantly a soluble form of mucin. Pleural effusions were obtained from breast cancer patients at Virginia Mason Hospital in Seattle, Wash. One sample (No. H3300) was composed of peritoneal fluid taken from a patient diagnosed as having metastatic lobular breast cancer. Sample No. H3422 was pleural effusion fluid from a patient originally diagnosed as having inflammatory breast cancer and who subsequently developed a moderate to well-differentiated infiltrating ductal adenocarcinoma. Another sample (No. H3415) consisted of pleural effusion fluid from patients diagnosed as having inflammatory breast cancer. The effusion fluids were stored frozen at −20° C.

Isolation of Mucins Obtained from Milk and Effusion Fluids

The preliminary technique used to purify mucins from milk and effusion fluids was a modification of the procedures of Creeth et al., *Biochem. J.*, 167, p. 557 (1977), incorporated by reference herein, as described by Linsley et al., supra. This procedure allowed preliminary purification of both MFGM-associated and soluble mucins, and prevented overloading the affinity chromatography columns used for final purification. Briefly, whole milk and effusion fluids were thawed, and guanidine HCl (United States Biochemical Corp., Cleveland, Ohio) was added to a final concentration of 6M. The mixture was stirred until clear. Equilibrium sedimentation in cesium chloride (CsCl) density gradients was then performed. CsCl (Bethesda Research Laboratories, Gaithersburg, Md.) was added at 0.6 g/ml (original volume) and the density was adjusted to 1.33–1.35 g/ml, measured gravimetrically. Samples were then centrifuged in a Beckman 50.2 rotor at 40,000 rpm (145,500× g average) for 60 to 65 hours at 21° C. Fractions were collected from the bottom of the tube and densities were measured. The fractions were dialyzed against $H_2O$ and then assayed for W1 inhibitory activity as described above. For the mucins derived from effusion fluids, peak fractions were pooled and subjected to a second centrifugation in a CsCl gradient containing 0.2M guanidine-HCl.

Affinity Chromatography

For final purification of mucins, affinity chromatography was performed. Peak fractions of W1 inhibitory activity from the CsCl gradients were mixed with antibody W9 (Dr. D. Ring, Cetus Corp., Emeryville, Calif.) conjugated to Sepharose 4B (Sigma Chemical Company, St. Louis, Mo.), at ratios of 200–3500 units/mg antibody in a solution of 50 mM NaCl buffered with 20 mM HEPES at pH 6.5. The W9 antibody was selected because W9 epitopes have been found on the same molecule as the W1 epitopes and because elution of bound mucin was achieved at a lower pH by using W9 than with the W1 antibody. Bound antigen was eluted as previously described by Linsley et al., *Biochemistry*, 25, p. 2978 (1986) incorporated by reference herein. Protein concentrations were determined as described by Markwell et al., *Anal. Biochem.*, 87, p. 206 (1979), incorporated by reference herein.

Tumor Pool Derived Mucin

Pools of tumor-derived mucin were purified from acid-ethanol extracted breast tumors provided by Dr. J. Rowe (Oncogen, Seattle, Wash.). Surgical specimens, the bulk of which were breast tumor tissue of a variety of histological classifications, were pooled and stored frozen at −70° C. Tumor tissue samples (45 g each) were thawed in a volume of 250 ml of extraction buffer (95% ethanol, 100 mM HCl, phenyl methyl sulfonyl fluoride (32 μg/ml), Aprotinin (2 mg/ml)), and the mixture was then stirred for 16 hours at 4° C. Insoluble material was collected by sedimentation at 10,000× g for 30 minutes at 4° C., resuspended in $H_2O$ at a concentration of approximately 4 g/ml (weight/volume) and guanidine HCl was immediately added to a final concentration of 6M. The mixture was vortexed vigorously and allowed to stand overnight at 4° C., then sedimented at 1,000× g for 10 minutes, and the supernatant was then collected, following removal of the lipid phase. CsCl density gradient centrifugation and affinity purification were performed as described above.

Sodium Dodecyl Sulfate-Polyacrylamide Gel Electrophoresis (SDS-PAGE)

To assess purity, SDS-PAGE was performed on aliquots of the CsCl gradient fractions of mucins which were found to exhibit W1 inhibiting activity. This procedure used 5–20% gradient polyacrylamide gels together with 4% stacking gels, as described by Linsley et al., *Biochemistry*, supra. Samples were analyzed under reducing conditions. Gels were stained using Coomassie Brilliant Blue destained, treated with 0.2% periodic acid for 40 minutes at 4° C., and then stained again using Schiff's Reagent (Sigma Chemical Co.) for 40 minutes at 4° C.

Amino Acid Analysis

Amino acid analysis of the affinity purified mucins obtained as described above was performed using standard techniques by Lowell H. Ericson (AAA Laboratories, Seattle, Wash.) following a 20 hour hydrolysis in 6N HCl at 115° C.

RESULTS

Biochemical Analysis of Purified Mucins

Mucins derived from milk and capable of binding W1 antibody (FIG. 1) banded in CsCl gradients at an equilibrium density of 1.38±0.01 (standard deviation), from a total of 7 experiments. This resulted in mucin purification of approximately 10-fold, with a yield of approximately 40%. The CsCl density gradient purification of mucins obtained from human milk, according to the above procedures, is shown in FIG. 2. Milk derived mucins band at a higher equilibrium density than the bulk of other milk proteins as seen by SDS-PAGE electrophoresis. Similar purification was achieved with mucins derived from pleural effusion fluids and the pooled acid-ethanol extracts from breast tumors.

Affinity purification of mucin from milk resulted in approximately 52% of the mucin antigenic activity in the pooled CsCl fractions (4 experiments) being recovered in the eluate; an approximately 400-fold purification of activity relative to whole milk. For pleural effusions, similar percentages of activity in the affinity column eluate were recovered, leading to an overall purification of about 2300-fold, with an overall yield of approximately 26%.

Figure 3:
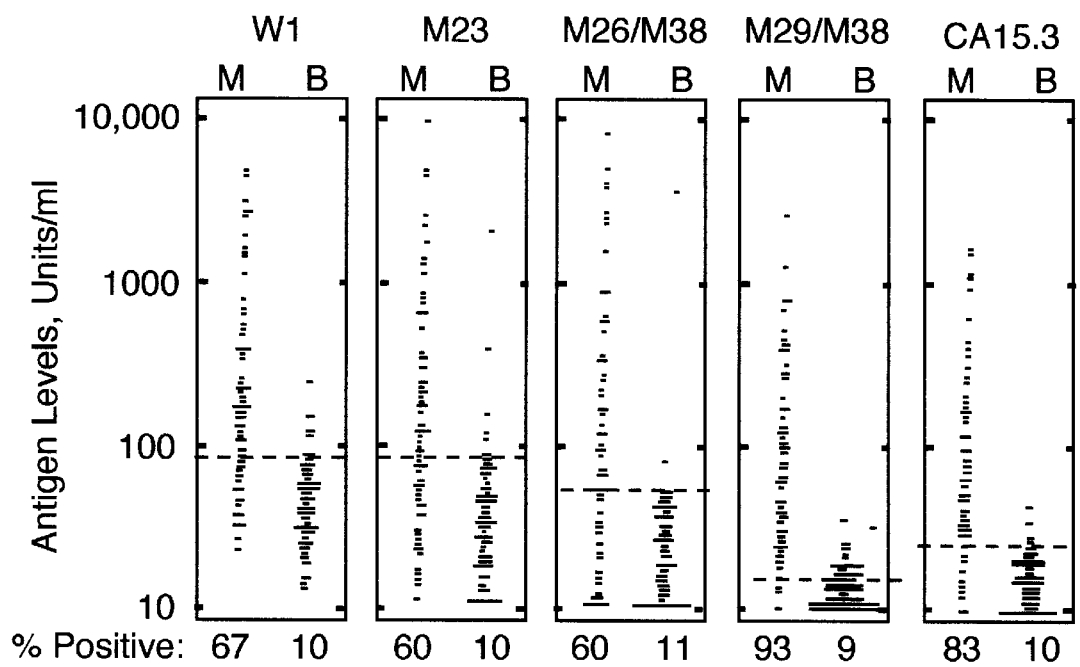
FIG. 3 is a photograph of SDS-PAGE gel analysis of affinity chromatography purified mucins from milk (lanes 2 to 5) and tumor tissues (lane 6=sample No. H3300 peritoneal effusion fluid breast tumor mucin; lane 7=sample No. H3415 pleural effusion breast tumor mucin; and lane 8=breast tumor pool mucin)
Figure 4:
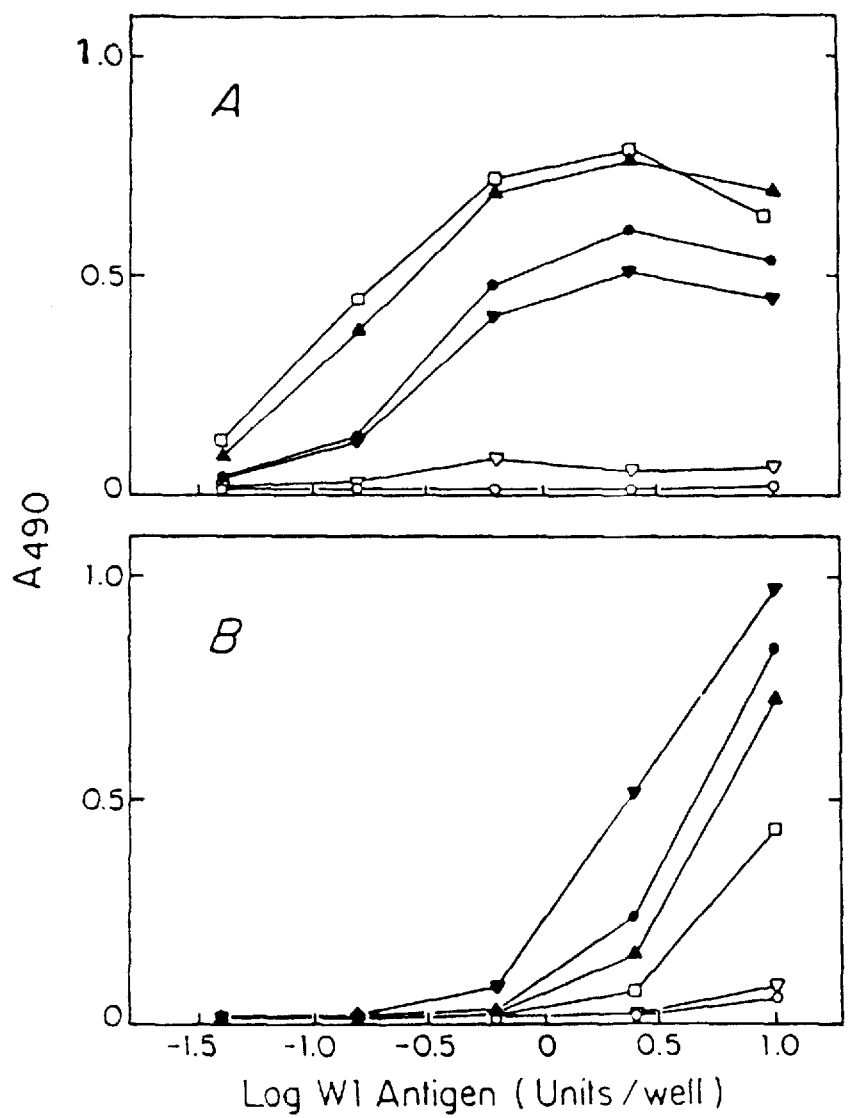
FIG. 4A/B shows dose-response curves for binding of monoclonal antibodies to purified mucins using the lectin-mucin capture assay described herein, 4A: milk mucin, 4B: pleural effusion mucin.

SDS-PAGE electrophoresis analysis of affinity purified mucin preparations obtained from milk or tumors (sample No. H3300 effusion, sample No. H3415 effusion, and pooled extracts from breast tumors) is shown in FIG. 3. The predominant components in all the mucin preparations were slow migrating, PAS-staining species, which bound the W1 antibody in immunoblotting experiments. In addition, all preparations contained low molecular weight contaminants of varying amounts and molecular weights, none of which react with the W1 antibody. Mucins from all three tumor-derived sources contain species which migrated as diffuse bands of approximately Mr=400,000. (Molecular weights given must be regarded as estimates since they are out of the range of the standards used and because of the high degree of glycosylation of these molecules.) Preparations from sample H3300 and the tumor pool were each resolved into two components of Mr=350,000 and 420,000, and 370,000 and 435,000, respectively. Mucins prepared from different milk samples show considerable variability in their migration during SDS-PAGE. The various components of these milk preparations which migrated at these varying rates showed no significant difference in immunoreactivity with any of the antibodies used herein.

Milk preparations Nos. 2 and 7 contained two diffuse species of relative molecular weight, Mr=335,000 and 480,000 for preparation No. 2, and 400,000 and 500,000 for preparation No. 7. Preparations No. 1 and 11 each contained only single diffuse species of Mr=450,000 and 380,000 respectively. No significant differences were observed in the immunoreactivity of the faster or slower migrating components with any of the antibodies used.

The amino acid composition of mucins purified from milk (preparation No. 2) and effusions (sample Nos. H3300, H3415 and H3422) are shown in Table 1. The amino acid composition of the glycoprotein PAS-O described by Shimizu et al., *J. Biochem. Tokyo*, 91, p. 515 (1982) is included in Table 1 for comparison. (The values determined for serine and threonine were corrected by 10% and 5% respectively, to compensate for destruction during hydrolysis.)

TABLE 1

AMINO ACID COMPOSITIONS OF PURIFIED MUCINS

| AMINO ACID (Mole %) | Milk 2 | H3300 | H3415 | H3422 | PAS-O |
|---|---|---|---|---|---|
| Ala | 10.9 | 14.5 | 16.8 | 17.6 | 13.0 |
| Arg | 3.2 | 3.4 | 5.2 | 5.5 | 3.9 |
| Asp | 7.4 | 4.4 | 5.6 | 6.0 | 6.4 |
| Cys | ND | ND | ND | ND | 0.5 |
| Glu | 9.0 | 5.7 | 5.5 | 6.0 | 8.3 |
| Gly | 13.9 | 9.2 | 9.8 | 11.8 | 12.2 |
| His | 3.4 | 2.9 | 3.9 | 2.9 | 3.8 |
| Ile | 2.7 | 0.9 | 1.2 | 1.6 | 1.9 |
| Leu | 5.2 | 1.9 | 3.2 | 3.6 | 3.7 |
| Lys | 3.1 | 3.6 | 2.4 | 2.3 | 2.2 |
| Met | ND | 0.4 | 0.4 | 0.0 | 0.8 |
| Phe | 1.9 | 0.7 | 1.2 | 1.4 | 1.7 |
| Pro | 15.2 | 18.6 | 15.9 | 14.1 | 12.0 |
| Ser | 9.1 | 8.1 | 10.7 | 10.3 | 13.1 |
| Thr | 9.5 | 14.6 | 11.2 | 10.8 | 9.8 |
| Tyr | 1.7 | 0.5 | 1.2 | 1.0 | 1.6 |
| Val | 5.4 | 10.3 | 5.8 | 6.5 | 5.3 |

ND = Not Determined

As shown in Table 1, although some differences in composition were observed, the overall amino acid compositions of both preparations were quite similar to each other and to the composition of PAS-O. The amino acids, alanine, glycine, proline, serine, and theonine, comprised 59 and 66% of the total for milk preparation No. 2 and effusion sample No. H3300, respectively. This compares with 65% for the same amino acids as determined for PAS-O.

EXAMPLE II

Generation of Monoclonal Antibodies to Mucins

Purified mucins obtained as described above were used to generate hybridomas for producing monoclonal antibodies to the mucins, and for characterizing the mucins.

Cells

Various human cancer cell lines were also used as immunogens to generate monoclonal antibodies reactive with mucins. Calu-1 lung carcinoma cells, which produce mucin antigens (available from the American Type Culture Collection (ATCC), Rockville, Md., No. HTB54), have been found to exhibit a characteristic, heterogeneous staining pattern when fluorescently labeled antibodies which recognize mucin antigen are bound to the cells. Calu-1 cells were used to derive new clonal cell lines W5-6, enriched for mucin antigen, and US-5 that produce low amounts of mucin antigen, as described by Linsley et al., *Cancer Research*, supra. Briefly, the Calu-1 cells were maintained in Dulbecco's Modified Eagle's Medium ("DMEM," GIBCO, Grand Island, N.Y.) supplemented with 10% fetal calf serum (FCS). Cell cloning was performed by limiting dilution in microtest wells. Care was taken to select clones derived from wells containing only single cells as judged using phase contrast microscopy. The derived cell lines, show the same isozyme phenotypes as Calu-1 cell lines, as determined by the Cell Culture Laboratory, (Children's Hospital, Detroit Medical Center, Detroit, Mich.). Monoclonal antibody W5 (described by Frankel et al., supra) was used to isolate derivatives of Calu-1 cells from cloning by fluorescent staining techniques using a fluorescent activated cell sorter (FACS). Cells that stained due to binding of the W5 antibody were then sorted by analyzing cells using the FACS and sterilely collecting the brightest cells (approximately 10% from 100–500,000 cells). The W5-6 cell line (Clone 6) was derived by limiting dilution analysis of W5S2 cells, a cell population obtained by twice sorting cells derived from Calu-1 cells that stained in response to binding of W5 antibody. The US-5 cell line was derived from unsorted Calu-1 cells (unenriched). The W5-6 cell line demonstrated elevated levels of W1, W5 and W9 antibody binding relative to the ability of the Calu-1 parental population to bind to these antibodies. Thus, the W5-6 cell line described herein is enriched in mucin antigen. In contrast, the US-5 cell line showed greatly decreased binding of the W1, W5 and W9 antibodies as compared to W5-6 or Calu-1 parental population. The W5-6 cell line described herein have been deposited with the ATCC, Accession No. CRL 9267. US-5 cells were used in the present invention as immunogen in an attempt to tolerize mice to nonmucin antigens and to enhance the reactivity of the monoclonal antibodies produced herein to mucin antigens.

MCF-7, a breast carcinoma cell line, was obtained from Dr. Marc Lippman (National Institute of Health, Bethesda, Md.) and used to generate monoclonal antibodies reactive with breast tissue associated mucin antigens.

Monoclonal Antibodies

In addition to the new monoclonal antibodies described herein, previously described monoclonal antibodies were also used in the following procedures for comparison with the new monoclonal antibodies. These antibodies were chosen because of their availability and their previously demonstrated reactivity with mucins from breast tumor or other malignant tissues. These antibodies are set forth in Table 2.

TABLE 2

PREVIOUSLY DESCRIBED MONOCLONAL ANTIBODIES

| ANTIBODY NAME | ANTIGEN/ EPITOPE |
| --- | --- |
| W1 | MUCIN |
| W9 | MUCIN |
| HMFG-1 | MUCIN |
| HMFG-2 | MUCIN |
| B72.3 | MUCIN |
| DUPAN-2 | MUCIN |
| CA 19-9 | Sialyated Lewis a |
| CO-51.4 | Lewis a |
| CO-30.1 | Lewis b |
| L15 | Lewis y |
| L17 | Lewis x |
| C6 | I |
| DF3 | MUCIN |

Antibodies W1 and W9 (Linsley et al., *Cancer Research*, supra; and previously referred to as 2G3 and 245E7 by Frankel et al., *J. Biol. Response Modifiers*, 4, p. 273–286 (1985)) were provided by Dr. David Ring (Cetus Corporation, Emeryville, Calif.). Antibodies HMFG-1 and HMFG-2 (Taylor-Papadimitriou et al., *Int. J. Cancer*, 28, p. 17 (1981)) were purchased from Unipath Limited (Bedford, England). Antibodies B72.3 (Colcher et al., *PNAS* (USA), 78, p. 3199 (1981)) and DUPAN-2 (Metzgar et al., *PNAS* (USA), 81, p. 5242 (1984)) were obtained from Drs. Jeffrey Schlom (NIH) and Richard Metzgar (Duke University, Raleigh, N.C.), respectively. The CA 19-9 antibody (Koprowski et al., *Somatic Cell Genetics*, 5, p. 957 (1979)), the CO-51.4 antibody (Blaszczyk et al., *Hybridoma*, 2, p. 240 (1983)) and the CO-30.1 antibody (Id.) were all obtained from the ATCC. Antibodies L15 and L17 (Hellstrom et al., *Cancer Research*, 46 p. 3917–3923 (1986)) were provided by Dr. I. Hellstrom (Oncogen, Seattle, Wash.). Antibody C6 (Fenderson et al., *Mol. Immunology*, 23, p. 747 (1986)) was provided by Drs. Bruce Fenderson and S. Hakomori (Fred Hutchinson Cancer Research Center (FHCRC), Seattle, Wash.). Antibody DF3 was supplied by Dr. D. Kufe (Harvard University, Cambridge, Mass.).

Antibodies B72.3 and DUPAN-2 were used as ascites fluid. Antibodies CA 19-9 and C6 were used as culture supernatants. All other antibodies were purified from ascites fluid.

New Monoclonal Antibodies

New hybridomas producing monoclonal antibodies reactive with the purified mucins, and producing at least one antibody capable of preferentially recognizing tumor-derived mucins were developed using several immunization protocols and screenings described below.

Mice used for immunizations were obtained from FHCRC or (Jackson Laboratories, Bar Harbor, Me.). After intraperitoneal (i.p.) or subcutaneous (s.c.) immunizations with MFGM, MCF-7, W5-6 cells, US-5 cells or purified mucins, as described below, the mice were boosted and three days following the boost, spleen cells were removed from the mice. Spleen cells were harvested and fused with NS-1 myeloma cells (Genetic Systems, Seattle, Wash.) using known fusion procedures to form the hybridoma. All hybridomas were cloned by limiting dilution. In some cases, to obtain more stable hybridoma cells, subcloning was performed. Hybridomas were deposited with the ATCC and accorded accession numbers as shown in Table 3 below. Hybridomas HB9248, HB9212, HB9210, HB9243, and HB9365 have been deposited pursuant to the Budapest Treaty on the International Recognition of the Deposit of Microorganisms for the Purposes of Patent Procedure with the Patent Culture Depository of the American Type Culture Collection (ATCC), 12301 Parklawn Drive, Rockville, Md. 20856 U.S.A.

Immunization Protocols

Hybridoma Producing Onc-M8 Monoclonal Antibody

Balb/c mice were immunized i.p. and s.c. with an injection of 225 $\mu$g of MFGM with Complete Freund's Adjuvant (CFA). Two weeks later, 270 $\mu$g of MFGM was injected i.p. without adjuvant. Twenty days later, 135 $\mu$g of MFGM was injected s.c. with Incomplete Freund's Adjuvant (IFA). Two months later, 200 $\mu$g of MFMG was injected i.p., without adjuvant. Immunized mice were boosted with 900 units of purified milk mucin i.p. eight days later.

Hybridomas Producing Onc-M10, Onc-M11, Onc-M12 and Onc-M15 Monoclonal Antibodies Balb/c mice were immunized i.p. with $1.2 \times 10^7$ MCF-7 cells using CFA. 28 days later, $1.2 \times 10^7$ MCF-7 cells were injected i.p. without adjuvant. 14 days later, $1.3 \times 10^7$ MCF-7 cells were injected i.p. without adjuvant. 24 days later, $1.2 \times 10^7$ MCF-7 cells were injected i.p. without adjuvant. Immunized mice were boosted prior to fusion approximately four months later with $4 \times 10^6$ MCF-7 cells and 100 $\mu$g of MFGM i.p.

Hybridomas Producing Onc-M16, Onc-M21 and Onc-M25 Monoclonal Antibodies (C57-B1/6×Balb/c)F1 hybrid mice (Onc-M16 and Onc-M25 were obtained from the same mouse; Onc-M21 was from a separately immunized mouse) were immunized i.p. and s.c. with $10^7$ W5-6 cells (Oncogen, Seattle, Wash.) without adjuvant. 17 days later, another injection of $5\times10^6$ W5-6 cells was administered i.p. and s.c., without adjuvant. Subsequently, 33 days later, $5\times10^6$ W5-6 cells were injected i.p. and s.c. without adjuvant. Immunized mice were boosted with $10^7$ MCF-7 cells and 100 μg MFGM 34 days i.p., without adjuvant, after the last injection.

Hybridomas Producing Onc-M22 and Onc-M23 Monoclonal Antibodies

Balb/c mice were immunized i.p. with $6.5\times10^6$ MCF-7 cells using CFA. 20 days later, $3.5\times10^6$ MCF-7 cells were injected i.p. using IFA and 125 μg of MFGM. 18 days later, $5\times10^6$ MCF-7 cells were injected i.p. without adjuvant. Immunized mice were boosted prior to fusion with 160 μg MFGM cells i.p.

Hybridoma Producing Onc-M26 Monoclonal Antibody

Balb/c mice were immunized i.p. with 250 units of CsCl gradient pleural effusion mucin, and 25 days later with 150 units i.p. and s.c. affinity purified pleural effusion mucin from a patient with breast cancer (sample No. H3300). In addition, an s.c. injection of $8\times10^6$ W5-6 cells was given 33 days following the first two pleural effusion injections. CFA was used with the first injection of pleural effusion mucin, and IFA was used with the subsequent injections of pleural effusion mucin. No adjuvant was used for the injection of W5-6 cells. Immunized mice were boosted 30 days later with 1000 units of SDS-PAGE gel purified pleural effusion mucin i.p. (the mucin band was excised from a polyacrylamide gel for injection) with IFA, then 500 units of CsCl gradient mucin 24 days later, followed by 1000 units of CsCl purified mucin i.p. 25 days later.

Hybridoma Producing Onc-M27 Monoclonal Antibody

NZB mice were immunized i.p. and s.c. without adjuvant, with three injections of $8.5\times10^6$ to $10^7$ W5-6 cells every three weeks. A boost was given after 23 days of $3\times10^6$ W5-6 cells and 200 μg of MFGM i.p. and s.c. without adjuvant.

Hybridomas Producing Onc-M29 and Onc-M30 Monoclonal Antibodies

Neonatal Balb/c mice (from Balb/c mice obtained from FHCRC) were immunized i.p. without adjuvant with one injection of $10^7$ US-5 cells, then three injections of $10^7$ to $2\times10^7$ W5-6 cells i.p. without adjuvant, each injection one week apart, followed two and one-half months later by one injection of $10^7$ W5-6 cells i.p., without adjuvant, and 310 units of CsCl gradient purified milk mucin s.c. Fifty-five days later, a boost injection of $5\times10^6$ W5-6 cells and 1000 units of CsCl gradient purified milk mucin was given prior to fusion, i.p. and s.c.

Hybridoma Producing Onc-M38 Monoclonal Antibody

Balb/c mice were immunized s.c. three times at three-week intervals with 800 units of affinity purified pleural effusion mucin from a patient with breast cancer (Sample No. H3415). The mucin was bound to poly-L-lysine-coated silica beads (0.007μ, Sigma Chemical Co., St. Louis, Mo.) prior to injection into the mice. Eighteen days after the third immunization with affinity purified effusion mucin, the mice were boosted with 4000 units of affinity purified mucin administered i.p.

The hybridomas producing these novel monoclonal antibodies, listed in Table 3 have been deposited in the ATCC, 12301 Parklawn Drive, Rockville, Md., USA 20851. The immunization protocols for the new antibodies developed herein and described above are summarized in Table 3. In addition, the deposited hybridoma cell lines and the monoclonal antibodies they produce are shown in Table 3.

TABLE 3

DESCRIPTION OF NEW ANTIBODIES

| MONOCLONAL ANTIBODY | ISOTYPE[1] | IMMUNOGEN[2] | ANTIGEN IDENTIFICATION[3] | ATCC NO. |
| --- | --- | --- | --- | --- |
| Onc-M8 | IgG1 | MFGM, Milk-Derived Mucin | IP, IB, DDIA | HB 9209 |
| Onc-M10 | IgG1 | MCF-7 cells, MFGM | IP, IB, DDIA | HB 9244 |
| Onc-M11 | IgG1 | MCF-7 cells, MFGM | IP, IB, DDIA | HB 9245 |
| Onc-M12 | IgG1 | MCF-7 cells, MFGM | IP, IB, DDIA | HB 9246 |
| Onc-M15 | IgG1 | MCF-7 cells, MFGM | IP, IB, DDIA | HB 9247 |
| Onc-M16 | IgG1 | W5-6 cells, MCF-7 cells, MFGM | IP, IB, DDIA | HB 9216 |
| Onc-M21 | IgG1 | W5-6 cells, MCF-7 cells, MFGM | IP, DDIA | HB 9248 |
| Onc-M22 | IgG1 | MCF-7 cells, MFGM | IP, IB, DDIA | HB 9249 |
| Onc-M23 | IgG1 | MCF-7 cells, MFGM | IP, IB, DDIA | HB 9250 |
| Onc-M25 | IgG1 | W5-6 cells, MCF-7 cells, MFGM | IP, IB, DDIA | HB 9217 |
| Onc-M26 | IgM | H3300 Mucin, W5-6 cells | IB, DDIA | HB 9212 |
| Onc-M27 | IgG2a | W5-6 cells, MFGM | IB, DDIA | HB 9229 |
| Onc-M29[4] | IgG1 | US-5 cells, W5-6 cells, Milk-Derived Mucin | IP, DDIA | HB 9243 HB 9210 |

TABLE 3-continued

DESCRIPTION OF NEW ANTIBODIES

| MONOCLONAL ANTIBODY | ISOTYPE[1] | IMMUNOGEN[2] | ANTIGEN IDENTIFICATION[3] | ATCC NO. |
|---|---|---|---|---|
| Onc-M30 | IgG1 | US-5 cells, W5-6 cells, Milk-Derived Mucin | DDIA | HB 9211 |
| Onc-M38 | IgG1 | Mucin | IP, IB, DDIA | HB 9365 |

[1]Isotypes were determined by the ELISA using class specified antibodies.
[2]Mice were immunized with MFGM, MCF-7, W5-6 cells and US-5, or purified mucin preparations as described above.
[3]Antigens recognized by the new monoclonal antibodies were identified by the following procedures: immune-precipitation (IP), immunoblot (IB), or double determinant immune assays (DDIA) as described in Example II.
[4]The data presented in Example II were obtained from a clone, hybridoma Onc-M29.41 (ATCC No. HB 9243). Subclone, Onc-M29 (ATCC No. HB 9210) was derived from a sister clone of Onc-M29.41 and was similarly characterized.

Screening

Various screening procedures were used to isolate hybridomas which produced monoclonal antibodies capable of binding to purified mucin antigens.

For detection of antibodies present in the hybridoma supernatants and capable of binding to purified mucins obtained as described above, a WGA capture assay was developed. In this procedure, purified mucins from pleural effusion or milk were immobilized on 96 well, flat bottom, polystyrene microtiters plates (Immulon II, Dynatech Laboratories, Inc., Alexandria, Va.) using *Tritium vulgaris* lectin (Wheat Germ agglutinin "WGA" from Sigma Chemical Co., St. Louis, Mo.). The microtiter® plates were prepared by the addition of 50 μl/well of a 20 μg/ml solution of WGA in 50 mM Tris-HCl containing $CaCl_2$, and 10 mM $MgCl_2$ at pH 8.0. Following a two hour incubation at 25° C. to coat the plates with WGA, the solution was removed by aspiration. After affinity chromatoqraphy, purified mucins were then added (1.0 inhibitory units (inhibition of W1 antibody binding to W1 antigen) per well unless otherwise indicated), in 50 mM Tris-HCl at pH 8, containing 1 mM $CaCl_2$ and 1 mM $MgCl_2$. The plates were then incubated for a period of from 1 to 4 hours at 25° C. and washed using buffer PBS and 2% FCS.

To conduct the assay, previously identified monoclonal antibodies were added at saturating concentrations (1 μg/ml) for purified antibodies, or at dilutions of 1:50 for ascites fluids. For assaying new antibodies, supernatants from hybridoma cultures were added undiluted to the plates.

Figure 2:
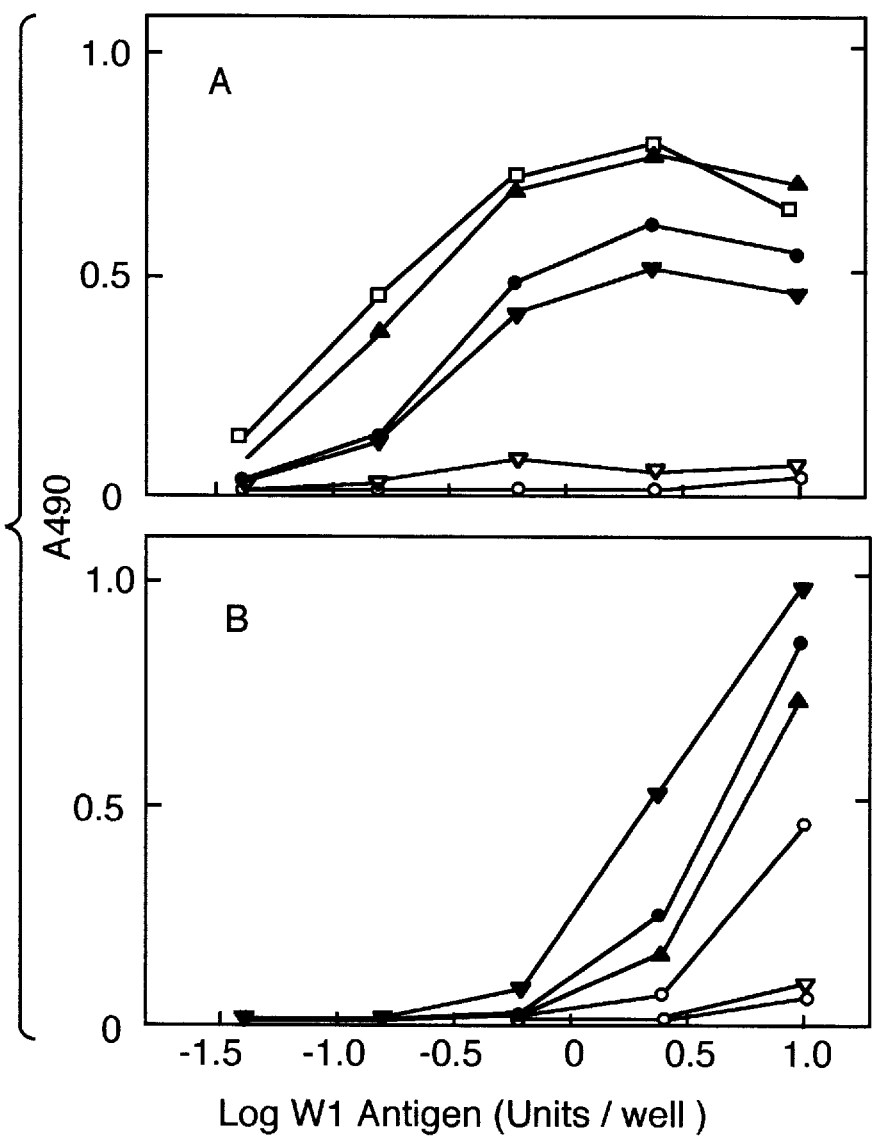
FIG. 2 is a photograph of a SDS-PAGE gel from CsCl density gradient purification of milk mucins.

The performance of the WGA assay was tested with increasing amounts of purified milk and effusion mucin in an experiment shown in FIG. 1. Dose-response curves for the binding of the W1 antibody were linear over more than a 10-fold range of inhibitory units per well for both milk and tumor pool-derived mucins, but the curve for the tumor-derived sample was shifted to the right and steeper. Other antibodies tested showed dose-response curves which were parallel to the curves for the W1 antibody but whose relative positions were shifted depending on the particular mucin source. These results indicate that epitopes recognized by the antibodies are expressed in different relative densities on mucins from normal and tumor sources.

An indirect enzyme immunoassay (ELISA) was used to detect antibody binding to purified mucin antigens immobilized using the WGA. (This procedure is referred to hereafter as "WGA capture assay".) Briefly, the binding of the novel monoclonal antibodies produced as described above was measured by addition of horseradish peroxidase (HRP)-conjugated goat anti-mouse immuno globulin (CAPPEL, Malvern, Pa.)(HRP) or by use of IgG specific goat anti-mouse antibody (Southern Biotek, Birmingham, Ala.) to reduce the number of IgM antibodies obtained.

For preliminary screening of the Onc-M8 hybridoma, supernatants were tested 9 days after fusion for binding to purified pleural effusion mucin using the WGA capture assay described above. For hybridomas that tested positive for binding, a secondary competition binding assay was performed using pools of normal and tumor serum.

The Onc-M10, Onc-M11, Onc-M12, and Onc-M15 hybridoma supernatants were first screened by testing in an ELISA assay for binding to live (unfixed) MCF-7 cells. For hybridoma supernatants testing positive, two secondary screens were performed. First, a competition binding assay was conducted using live MCF-7 cells in which each hybridoma supernatant was tested for antibody capable of binding to the cells. Secondly, supernatants were screened to detect binding to purified milk mucin bound to plates using polylysine.

For preliminary screening of the Onc-M16 and Onc-M25 hybridomas supernatants from fusion of myeloma cells with spleen cells from immunized mice were tested for binding to paraformaldehyde fixed W5-6 cells. The binding assay was performed on paraformaldehyde fixed cell monolayers as described by Linsley et al., in *Biochemistry*, supra. For hybridomas testing positive a secondary screen was performed by observing the fluorescent staining pattern of binding of antibody to Calu-1 cells.

The Onc-M21 hybridoma was preliminarily screened by testing for binding against polylysine-adhered MFGM using the ELISA. For the hybridomas testing positive, a secondary screen was performed using the WGA capture assay to detect binding using tumor and normal sera.

For the Onc-M22 and Onc-M23 hybridoma supernatants from fusion of myeloma cells with spleen cells from immunized mice were preliminarily screened 11 and 13 days after fusion. The WGA capture assay was used to detect any antibody present in the hybridoma supernatant capable of binding preferentially to tumor than to normal sera samples.

For the Onc-M26 hybridoma supernatant from fusion of myeloma cells with spleen cells from immunized mice were preliminarily tested 7 days after fusion by binding to purified pleural effusion mucin captured by lectin using the WGA binding assay. Where binding was detected, the WGA-ELISA assay was then used to compare the ability of the hybridoma supernatant to bind to WGA-captured mucin present in serum obtained from patients with tumors as compared to normal serum.

The Onc-M27, Onc-M29 and Onc-M30 hybridoma supernatants were tested seven days after fusion by binding to CsCl purified milk mucin derived, as described above, using the WGA capture assay. Hybridoma supernatants testing positive were re-assayed on affinity purified milk mucin using the WGA-ELISA assay. Hybridoma supernatants were also screened by comparing binding to IgG and IgM specific goat anti-mouse antibodies; generally, those found to be specific for IgG were selected for further characterization.

The Onc-M38 hybridoma supernatant was screened for the presence of antibody by binding to gradient purified pleural effusion mucin captured by lectin using the WGA binding assay. The hybridoma supernatants that tested positive were retested in the WGA binding assay using gradient and affinity purified pleural effusion mucin.

Hybridoma supernatants producing monoclonal antibodies that bound to mucin antigen (purified antigen or cell-associated) as described above were injected into pristane-primed mice to produce ascites fluid from which the monoclonal antibodies were purified using known purification procedures. Following ammonium sulfate precipitation, IgG antibodies were purified by ion exchange on DEAE Sephacel columns (Pharmacia, Uppsala, Sweden) and the IgM antibody (M26) was purified using size fractionation on a Sephacryl S-300 column (Pharmacia). Isotypes (immunoglobulin subclasses of the antibodies) of purified antibodies were determined by an enzyme immunoassay (described below) using class specific antibodies (Southern Biotek).

EXAMPLE III

Characterization of New Monoclonal Antibodies

The new antibodies isolated as described above, were tested for their abilities to bind to all of the purified mucins using the WGA capture assay described above. A single concentration of 1.5 inhibitory units of antigen was used per well, and saturating concentrations of antibody (1 μg/ml) were employed. The substrate incubation was stopped when the maximal O.D. values for each sample were in the range of 0.4 to 1.4.

Several additional procedures were used to demonstrate that the new antibodies recognized mucin antigen which also bound the W1 antibody. These procedures were immune precipitation (IP) from tumor cell extracts labeled with either $^3$H-glucosamine or $^3$H-threonine; and immunoblots (IB) on purified mucins or cell membrane preparations as described by Linsley et al., Biochemistry, 25, p. 2978 (1986). A double determinant immunoassy (DDIA) was also used, in which antibodies were tested for their ability to capture mucins which bound to HRP-conjugated W1 antibody (Table 3).

The new antibodies were also tested for binding to paraformaldehyde-fixed cultured W5-6 cell lines as described in Linsley et al., Biochemistry, 25, p. 2978 (1986).

RESULTS

Antibody Bindinq to Purified Mucin Antigen

The monoclonal antibodies produced herein react with mucins from human milk, tumor cell lines, pleural effusion fluids and tumors, as determined by the WGA capture assay and DDIA binding assays described above. Most of the novel antibodies described herein reacted with mucins as determined by using more than one procedure; however, the DDIA procedure alone was used for antibody Onc-M30. Since the purified mucins contain the W1 epitope (see Table 4), then the new antibodies react with either the W1 epitope or what appear to be novel epitopes on mucin antigens. These antibodies may also bind to additional epitopes on mucin antigens, such as the T and Tn epitopes.

TABLE 4

ANTIBODY BINDING TO PURIFIED MUCINS[1]

| MUCIN SOURCE: | BREAST TUMORS | | | | | | |
|---|---|---|---|---|---|---|---|
| ANTIBODY | H3300 | H3415 | TUMORS | MILK 1 | MILK 2 | MILK 7 | MILK 11 |
| NONE | 0.011[1] | 0.028 | 0.008 | 0.010 | 0.012 | 0.013 | 0.049 |
| PREVIOUSLY DESCRIBED ANTIBODIES | | | | | | | |
| W1 | 0.891 | 0.959 | 0.408 | 0.767 | 0.629 | 0.815 | 0.983 |
| W9 | 0.289 | 0.353 | 0.099 | 0.609 | 0.566 | 0.635 | 0.840 |
| HMFG-1 | 0.036 | 0.177 | 0.052 | 0.520 | 0.492 | 0.597 | 0.796 |
| HMFG-2 | 0.020 | 0.158 | 0.030 | 0.420 | 0.327 | 0.328 | 0.533 |
| C6 | 0.017 | 0.050 | 0.021 | 0.538 | 0.418 | 0.483 | 0.529 |
| CO-51.4 | 0.012 | 0.033 | 0.013 | 0.160 | 0.016 | 0.128 | 0.393 |
| L-17 | 0.012 | 0.030 | 0.013 | 0.150 | 0.013 | 0.136 | 0.246 |
| B72.3 | 0.032 | 0.088 | 0.041 | 0.022 | 0.022 | 0.022 | 0.051 |
| DUPAN-2 | 0.052 | 0.102 | 0.058 | 0.035 | 0.035 | 0.029 | 0.059 |
| CA 19-9 | 0.013 | 0.034 | 0.013 | 0.020 | 0.021 | 0.020 | 0.045 |
| CO-30.1 | 0.011 | 0.028 | 0.012 | 0.027 | 0.013 | 0.050 | 0.047 |
| L15 | 0.011 | 0.034 | 0.012 | 0.012 | 0.011 | 0.014 | 0.044 |
| NEW ANTIBODIES | | | | | | | |
| Onc-M8 | 0.079 | 0.671 | 0.140 | 1.050 | 1.048 | 1.031 | 1.318 |
| Onc-M10 | 0.071 | 0.122 | 0.057 | 0.031 | 0.028 | 0.031 | 0.062 |
| Onc-M11 | 0.014 | 0.051 | 0.020 | 0.011 | 0.013 | 0.015 | 0.043 |
| Onc-M12 | 0.030 | 0.141 | 0.088 | 0.020 | 0.016 | 0.020 | 0.058 |
| Onc-M15 | 0.013 | 0.118 | 0.015 | 1.086 | 0.610 | 0.888 | 1.093 |
| Onc-M16 | 0.273 | 0.355 | 0.199 | 1.180 | 0.871 | 0.978 | 1.135 |
| Onc-M21 | 0.012 | 0.033 | 0.014 | 0.050 | 0.024 | 0.030 | 0.116 |
| Onc-M22 | 0.011 | 0.070 | 0.014 | 1.286 | 0.825 | 1.071 | 1.380 |
| Onc-M23 | 0.014 | 0.206 | 0.024 | 1.404 | 0.707 | 1.054 | 1.334 |
| Onc-M25 | 0.071 | 0.094 | 0.067 | 0.937 | 0.671 | 0.890 | 0.902 |
| Onc-M26 | 0.402 | 0.047 | 0.023 | 0.034 | 0.023 | 0.019 | 0.055 |
| Onc-M27 | 0.029 | 0.091 | 0.015 | 0.370 | 0.246 | 0.209 | 0.283 |

TABLE 4-continued

ANTIBODY BINDING TO PURIFIED MUCINS[1]

MUCIN SOURCE: BREAST TUMORS

| ANTIBODY | H3300 | H3415 | TUMORS | MILK 1 | MILK 2 | MILK 7 | MILK 11 |
|---|---|---|---|---|---|---|---|
| NONE | 0.011[1] | 0.028 | 0.008 | 0.010 | 0.012 | 0.013 | 0.049 |
| Onc-M29 | 0.014 | 0.031 | 0.013 | 0.065 | 0.022 | 0.040 | 0.159 |
| Onc-M30 | 0.013 | 0.031 | 0.012 | 0.053 | 0.021 | 0.036 | 0.156 |

[1]Measurements are in units of absorbance, O.D.$_{490}$

As can be seen from Table 4, some monoclonal antibodies (Onc-M8, Onc-M16, W1, and W9) gave high absorbance values ($\geq 0.1$), binding to the majority of samples from milk and tumor sources; certain antibodies (Onc-M15, Onc-M22, Onc-M23, Onc-M25 and Onc-M27, HMFG-1, HMFG-2, gave high absorbance values ($\geq 0.1$), binding to the majority of milk mucins but not to tumor derived samples; and other antibodies (Onc-M10, Onc-M11, Onc-M12, Onc-M21, Onc-M29, Onc-30 and B72.3 DUPAN-2, CA19-9), gave absorbance values of <0.1 failing to bind to the majority of samples from either milk or tumor sources. Antibody Onc-M26, bound strongly to pleural effusion mucin (sample H3300) but bound weakly to all milk-derived mucin samples. Note that although certain antibodies did not bind significantly to the pleural effusion or breast tumor mucins in the direct binding assay, binding of all antibodies to mucin epitopes on pleural effusion mucin sample H3300 was detected by the more sensitive DDIA. Onc-M38 was not tested in this assay, but in a separate experiment gave high absorbance values for binding to both milk and effusion mucin.

The mucins purified from the milk of several donors were found to be antigenically similar, suggesting that the antibodies tested do not detect polymorphic antigenic determinants such as blood group antigens (e.g., ABO and Lewis). Although 80% of the population are Lewis-positive (and two of the milk donors, 1 and 7, were shown by saliva testing to be Lewis-positive), none of the tumor-derived mucins had levels of Lewis antigens detectable by the binding assay. None of the milk mucin preparations (including samples 1 and 7) had detectable levels of Lewis b (antibody CO-30.1) or Lewis y (antibody L15), while three of them (including samples 1 and 7) had detectable, though low, levels of Lewis a (antibody CO-51.4) and Lewis x (antibody L17). This suggests that Lewis antigens are expressed only weakly in milk mucin and very little, if at all, in the mucin derived from breast carcinomas. In contrast, these epitopes have been detected on mucin antigens from colon carcinomas. Magnani et al., *Cancer Research*, 43 p. 5489 (1983) and Johnson et al., *Cancer Research*, 46, p. 850 (1986).

When compared with the milk mucins, the tumor-derived mucins exhibited quite different antibody binding profiles. The data suggest that monoclonal antibodies recognizing new mucin epitopes were identified using the process of the present invention. W1 antibody bound to all tumor-derived samples, to a relatively higher degree than the other antibodies tested, i.e., relative to W1, binding of all other antibodies was reduced.

One of the new antibodies described herein, Onc-M26, produced by hybridoma cell line ATCC No. HB 9212, detected the most "tumor specific" epitope. This epitope was also detected on the other tumor-derived samples when higher concentrations of mucins were used in the assay, but a much lower level on mucins from milk samples. Onc-M26 thus shows promise as a monoclonal antibody capable of distinguishing between the presence of normal and cancer-tissue associated mucins in serum from a human subject in assays to detect cancer.

These data establish that the specificities of most of the new antibodies are different from those of the previously described antibodies. However, epitopes on antibodies Onc-M21 and Onc-M29 could not be distinguished from those of other antibodies such as B72.3 and DUPAN 2 based on these data, because they did not bind significantly to the purified mucin sources in the assay. The W5-6 cell binding experiments showed that Onc-M21 and Onc-M29 bound preferentially to the W5-6 cell line, as compared to the previously known antibodies, demonstrating the unique specificity of these antibodies.

These results demonstrate that purified mucins derived from tumor sources using the procedures described herein are immunologically distinct from mucins from normal breast epithelium present in milk. The data also suggests that antigenic epitopes present on mucins from normal breast epithelium tissue may be masked by other determinants, or may be present at reduced levels on mucins obtained from tumors. This, in turn, indicates that tumor mucins may contain epitopes not found on mucins from normal sources. Therefore, purified mucins including tumor-derived mucins may provide an improved immunogen for the development of monoclonal antibodies capable of recognizing mucin antigen, particularly those antibodies capable of reacting preferentially with tumor-derived mucins as compared to mucins from normal sources.

EXAMPLE IV

Serum Assay Using Monoclonal Antibodies M26 and M29

To demonstrate the usefulness of the monoclonal antibodies described herein, a DDIA was performed using the monoclonal antibodies Onc-M26 and Onc-M29 obtained as described in Example II. The W1 antibody was used for comparison.

Immulon II plates were incubated with 50 µl/well of 10 µg/ml of Onc-M26, or Onc-M29 antibody in 50 mM Tris buffer, pH 8.0, for one hour to coat the plates with antibody ("capture antibody"). The plates were then aspirated and blocked using 350 µl/well of blocking buffer (0.5% bovine serum albumin (BSA), 5% sucrose and 5% and Tris buffer) for one hour to overnight. The plates were again aspirated and blotted using paper towels, overnight. The plates were stored dry in plastic wrap at room temperature. Sera derived from patients diagnosed as having cancer and control sera (from normal patients) was diluted using fetal calf serum (FCS). When the assay was conducted using the monoclonal antibody Onc-M26 and the W1 antibody for detection of the capture antibody, both serum and controls were diluted in a ratio of 1:8. For the assay using monoclonal antibody M29 and W1 antibody, the serum and controls were diluted to a ratio of 1:50. The absorbance standards for Onc-M26 monoclonal antibody were made by volumetrically diluting a pleural effusion sample (No. H3375) prepared as described above in a mixture of pooled sera and FCS. Absorbance standards for the Onc-M29 antibody were made by diluting sample No. H3375 in FCS. Absorbance standards were calibrated by assigning the pools of sera a value of 20 absorbance units per ml. Controls consisted of pooled sera derived from Oncogen employees, and two breast pleural fusion samples. Both standards and controls were aliquoted and stored at −70° C.

50 µl of diluted sera, controls and standards was pipetted onto duplicate coated wells. Wells were sealed with plate sealer and incubated at room temperature for one hour. The plates were then manually rinsed twice using 2% FCS in phosphate buffered saline (PBS) buffer. 50 µl of an appropriate dilution of W1-HRP conjugated antibody was added to the plates. For the M26 assay, a concentration of 0.5 µg/ml of W1 HRP was used. For the M29 assay, 0.1 µg/per ml of the W1 HRP conjugate was found to be optimal. All conjugates were diluted in 2% FCS and PBS. The plates were then resealed and incubated for one hour at room temperature. The plates were subsequently manually rinsed three times using PBS buffer. 100 µl of OPD substrate was added to the plates, which were then incubated in the dark for one hour. Reactions were stopped using 50 µl of 1.5N sulfuric acid. Absorbance was read at 490 nm. Duplicates greater than 10 units/ml apart (or two units/ml if less than 10 units/ml) were repeated. Samples providing high results were diluted and retested. The assays were compared in terms of their ability to discriminate between the two groups of patients (with and without cancer). Cutoff values (units/ml) were selected to give approximately 90% specificity (i.e. 90% of the control group tested negative). The results are depicted in Table 5.

TABLE 5

| | Test Cutoff (units/ml) | Serum Assay % Above Cutoff | | | | | | | |
|---|---|---|---|---|---|---|---|---|---|
| | | 0[a] | 1 | 2 | 3 | 4 | 5 | 6 | Control |
| W1[b] | 115 | 3.1 | 6.8 | 11.4 | 57.8 | 0.5 | 2.9 | 7.2 | 4.0 |
| M26 | 95 | 4.3 | 5.7 | 11.4 | 43.1 | 0.0 | 0.0 | 1.1 | 0.5 |
| M29 | 60 | 5.5 | 11.4 | 18.2 | 66.4 | 1.5 | 2.2 | 6.8 | 4.0 |
| M26 | 95(M26) | 8.0 | 14.8 | 22.7 | 75.0 | 1.5 | 2.2 | 7.6 | 4.3 |
| M29[c] | 60(M29) | | | | | | | | |

[a]Sera Tested

| Code | Description | Number of Samples |
|---|---|---|
| 0 | No Evidence of Disease | 163 |
| 1 | Primary | 88 |
| 2 | Regional | 88 |
| 3 | Metastatic | 116 |
| 4 | Healthy | 202 |
| 5 | Breast Disease | 138 |
| 6 | Benign Disease | 264 |

| [b]Test Name | Immobilized Capture Antibody | HRP-Labeled Secondary Detecting Antibody |
|---|---|---|
| W1 | W1 | W1-HRP |
| M26 | Onc-M26 | W1-HRP |
| M29 | Onc-M29 | W1-HRP |

[c]These values represent those percentages of the sample ranked positive for either the M26 or M29 test.

Table 5 shows the results of the DDIA assay using sera from cancer patients, with the monoclonal antibody W1, and new monoclonal antibodies Onc-M26 and Onc-M29. The test column indicates which monoclonal antibodies were used with the W1 monoclonal antibody in the DDIA as described above. In the W1 test (homologous DDIA) the W1 monoclonal antibody was immobilized as the capture antibody to bind mucin antigen present in the serum from the human subject. The secondary detecting antibody used in these tests was W1 antibody conjugated with HRP. In the M26 test, the immobilized antibody was Onc-M26 and in the M29 test, Onc-M29 antibody was immobilized. The numerals following the antibody designation in the cutoff column indicate the level of antigen in units/ml above which the assay was determined to be positive for the presence of tumor-associated mucin. Columns 0–6 indicate the percentage of patients for that cancer type found to have a W1 epitope level above the level indicated in the cutoff column, as determined using the antibodies indicated. The control column indicates the percentage of assays of control sera (from patients without cancer) having a positive reaction (i.e., detecting the level of antigen indicated in the cutoff column, so-called "false positive" results). The number of patients in each category of sera (0–6) and the type of cancer present in these patients is also indicated in Table 5. Thus, where Onc-M26 was the capture antibody, with an antigen cutoff level of greater than 95 units/ml, approximately 43% of the 116 patients having metastatic cancer were identified as having cancer using the Onc-M26 capture antibody and W1 detecting antibody in the assay. Only 0.5% controls were erroneously detected as having cancer (false positives). Use of Onc-M29 antibody resulted in 66% of the patients correctly identified with 4% false positive identification. When W1 antibody was used as the primary and secondary antibody in the assay, approximately 58% of the 116 patients were identified as having cancer, but with 4% false positive identification.

Thus, use of the Onc-M29 antibody in the DDIA correctly identifies the presence of cancer in a larger fraction of cancer patients than does the W1 antibody, indicating an increased sensitivity of Onc-M29 used as a capture antibody, over the W1 antibody. The use of the Onc-M26 antibody results in a somewhat less sensitive assay than that using the Onc-M29 antibody. However, when compared to the W1 antibody, a very low number of false positives (0.5%) are observed and, thus, the assay is more specific. Assessing the positive results for the M26 or M29 tests provides a more sensitive indication of the presence of cancer than using the results of either the M26 or M29 test alone (for example, 75% of patients having metastatic cancer are ranked as positive). These results demonstrate the potential usefulness of the Onc-M26 and Onc-M29 monoclonal antibodies in the detection of cancer in human sera.

EXAMPLE V

Cross-Competition Analysis of Mucin Antibody Binding

The monoclonal antibodies of the present invention have been further characterized by cross-competition studies, the results of which are set forth in Table 6 below. These studies ascertained the concentration of unlabeled mucin antibody that resulted in one-half (50%) maximal inhibition of binding of a standard concentration (0.5 µg/ml) of $^{125}$I-labeled mucin antibody. A cross-competition analysis was carried out between each of the labeled ($^{125}$I) antibodies identified in Table 6 and each of the unlabeled antibodies designated across the top of Table 6. The competitive binding of antibodies M8, M15, M16, M22, M23, M25, M27, W1, W9 and M38 was measured on CsCl purified milk-derived mucin, whereas the binding of antibodies M10, M11, and M12 was determined with respect to the MCF7 cell line. The binding of Onc-M21 and Onc-M29 was determined with respect to the W5-6 cell line. Binding of $^{125}$I-labeled antibody at 0.5 μg/ml was measured in the presence of increasing amounts of unlabeled antibodies, up to 50 μg/ml. (M26 antibody was not included in this analysis because after radiolabeling it bound poorly to immobilized mucin).

In Table 6, the designation "++++" signifies that half maximal inhibition occurred at a concentration of unlabeled antibody of less than 3.2 μg/ml; the designation "+++" signifies that the quantity of unlabeled antibody required to give half maximal inhibition was between 3.2 and 15.8 μg/ml; the designation "++" signifies that the concentration of unlabeled antibody required to give half maximal inhibition of binding of the labeled antibody was between 16 and 31 μg/ml; the designation "+" signifies that the concentration of unlabeled antibody required to give half maximal inhibition of binding to the labeled antibody was from between 32 and 50 μg/ml; and, the designation "-" signifies that the concentration of unlabeled antibody required to give half maximal inhibition of binding of the labeled antibody was greater than 50 μg/ml.

and M38. However, antibody M10 did not compete significantly for binding of antibody W1 even when tested on MCF7 cells to which this antibody bound best.

The remaining antibodies showed patterns of cross-competition which suggested structural or spatial relationships between their respective epitopes. For example, epitopes for antibodies W9, M8, M16, and M25 appear to be related, as do those for M11 and M12.

Antibodies M15, M22, M23, and M27 also showed similar patterns of cross-competition, although some differences were observed. In general, these antibodies bind epitopes which appear to be structurally or spatially related to each other. Biochemical data suggests that these antibodies recognize core protein epitopes (see below). Based on cross-competition data, epitopes for these four antibodies are related to the epitope for antibody W1, and antibodies M22 and M23 are also related to the eptitope for M38.

In summary, the patterns of cross-competition between the new antibodies, and W1 and W9, indicated the presence of several epitopes on mucin molecules. Antibodies M21 and M29 recognize epitopes which are either identical or closely related, and are distinct from those recognized by other antibodies. All other antibodies recognize epitopes which share structural features, or are sterically related to

TABLE 6

CROSS-COMPETITION ANALYSIS OF MUCIN ANTIBODY BINDING

| | \multicolumn{15}{c}{UNLABELED ANTIBODY} | | | | | | | | | | | | | | |
|---|---|---|---|---|---|---|---|---|---|---|---|---|---|---|---|
| | W1 | W9 | M8 | M10 | M11 | M12 | M15 | M16 | M21 | M22 | M23 | M25 | M27 | M29 | M38 |
| $^{125}$I ANTIBODY | | | | | | | | | | | | | | | |
| W1 | +++ | - | - | - | - | - | - | - | - | - | - | - | - | - | - |
| W9 | - | +++ | +++ | - | - | - | - | +++ | - | - | - | ++ | - | - | ++++ |
| M38 | - | - | - | - | - | - | - | - | - | - | - | - | - | - | ++++ |
| M8 | - | ++ | +++ | - | - | - | - | +++ | - | - | - | + | - | - | ++++ |
| M16 | - | - | +++ | - | - | - | - | ++++ | - | - | - | ++ | - | - | ++++ |
| M25 | - | ++ | +++ | - | - | - | - | ++++ | - | - | - | +++ | - | - | - |
| M15 | +++ | - | - | - | - | - | ++++ | - | - | ++++ | +++ | - | ++ | - | ++++ |
| M22 | +++ | - | - | - | - | - | ++ | - | - | +++ | +++ | - | - | - | ++++ |
| M23 | +++ | - | - | - | - | - | ++++ | +++ | - | ++++ | +++ | - | +++ | - | ++++ |
| M27 | +++ | - | - | - | - | - | ++ | - | - | +++ | +++ | - | + | - | - |
| M10 | ++++ | - | ++++ | +++ | - | - | - | +++ | - | - | - | - | - | - | +++ |
| M11 | ++++ | - | - | - | ++++ | ++++ | - | - | - | - | - | - | - | - | - |
| M12 | ++++ | - | - | - | +++ | ++++ | - | - | - | - | - | - | - | - | - |
| M21 | - | - | - | - | - | - | - | - | ++++ | - | - | - | - | ++++ | - |
| M29 | - | - | - | - | - | - | - | - | ++++ | - | - | - | - | ++++ | - |

With respect to the results of the cross-competition analysis set forth in Table 6, several antibodies showed unique patterns of cross-competition, indicating that they bound to distinct epitopes. The most unique pattern of cross-competition was shown by antibodies M21 and M29 which competed for binding of each other, but neither competed for nor were competed by any of the other antibodies tested. These antibodies therefore recognize either the same or spatially related epitopes which are different from those recognized by the other antibodies.

Antibodies W1 and M38, were not competed for by any other antibodies, but they in turn, competed for binding of many other antibodies. This suggests that epitopes for these antibodies are distinct, but are either structurally similar or spatially related to those for other antibodies. Antibody M10 was competed for by several other antibodies, but in turn competed only for binding of $^{125}$I-M10, suggesting that it, too, bound to a distinct epitope which was structurally or spatially related to the ones for antibodies W1, M8, M16, epitopes for other antibodies. Antibodies W1, M10, and M38 recognize epitopes which are related to, but not identical to those of other antibodies. Antibodies M11 and M12 recognize a closely related epitope(s) which is also not identical to that recognized by other antibodies. M38 monoclonal antibody identifies a novel epitope not recognized by the other novel monoclonal antibodies of the present invention or by the W1 or W9 antibodies. From the foregoing, it appears that the Onc-M38 monoclonal antibody exhibits high specificity to a unique epitope on mucin antigens, and thus can serve an important function not only in assays for detecting tumors in patients, but also in the treatment of such tumors using the techniques and procedures discussed above.

EXAMPLE VI

Biochemical Characterization of Epitopes

In order to determine the biochemical nature of epitopes recognized by new antibodies, the effects of various treatments on antibody binding to mucins were studied.

To determine whether carbohydrate structures were required for binding of the antibodies, the effects of sodium periodate treatment on antibody binding were examined (Table 7). Mucins were immobilized on microtiter plates by WGA as described above and treated with sodium periodate (NaIO$_4$) at concentrations ranging from 0.2 to 100 mM in a buffer of 50 mM sodium acetate, pH 4.5, for a period of 30 minutes at 37° C. The Milk 2 derived mucin sample was affinity purified using antibody W9 and the H3300-derived mucin sample was CsCl purified. Mucins from MCF7 and W5-6 cell membranes were solubilized with a non-ionic detergent solution (TNEN, Linsley et al., *Biochem*, 25:2778–2986 (1986)) and separated from detergent insoluble material by centrifugation (390,000× gmin) prior to immobilization. Wells were washed thoroughly with PBS and treated with NaBH$_4$ (100 mM in PBS) for an additional 30 minutes at 37° C. Following treatments, wells were blocked with binding buffer described by Linsley et al, *Biochem*. 25:2978–2986 (1986), incorporated by reference herein, containing 10% FCS, and were tested for antibody binding by indirect ELISA. The concentration of NaIO$_4$ required to reduce binding by 50% was determined by interpolation from determined values.

The binding of a control antibody (C6) to a defined carbohydrate epitope (I structure) was sensitive to periodate treatment, with a half-maximal inhibition of binding occurring at 1 mM. Antibodies W1 and W9, and M26 were more sensitive to periodate treatment than was the control antibody; this sensitivity of W1 and W9 has been previously demonstrated, and suggests that carbohydrate is required for binding of these antibodies. Five other antibodies (M10, M11, M12, M21, and M29) were periodate sensitive, but required significantly higher concentrations than the control antibody. The remaining eight antibodies were insensitive to periodate treatment, even at extremely high concentrations (0.1M). Thus, epitopes for all of the new antibodies except M26 were less sensitive to periodate oxidation than antibodies W1 and W9, and the control antibody, C6.

TABLE 7

Effects of Periodate Treatment on Binding of Antibodies

| Antibody | Mucin | CONCENTRATION FOR HALF-MAXIMAL REDUCTION (mM) |
|---|---|---|
| Control | | |
| C6 | MILK 2 | 1 |
| VERY SENSITIVE | | |
| W1 | MILK 2 | 0.2 |
| W9 | MILK 2 | <0.2 |
| M26 | H3300 | <0.2 |
| INTERMEDIATE SENSITIVITY | | |
| M10 | MCF7 | 4 |
| M11 | MCF7 | 51 |
| M12 | MCF7 | 78 |
| M21 | W5-6 | 10 |
| M29 | W5-6 | 64 |
| RESISTANT | | |
| M8 | MILK 2 | >100 |
| M15 | MILK 2 | >100 |
| M16 | MILK 2 | >100 |
| M22 | MILK 2 | >100 |
| M23 | MILK 2 | >100 |
| M25 | MILK 2 | >100 |

TABLE 7-continued

Effects of Periodate Treatment on Binding of Antibodies

| Antibody | Mucin | CONCENTRATION FOR HALF-MAXIMAL REDUCTION (mM) |
|---|---|---|
| M27 | MILK 2 | >100 |
| M38 | MILK 2 | >100 |

To test whether sialic acid was required for antibody binding, antibodies were tested for sensitivity to neuraminidase in the experiment summarized in Table 8. Mucins were immobilized on microtiter plates by WGA and treated with neuraminidase from *Vibrio cholerae* as described by Linsley et al., *Cancer Res*. 46, supra. Neuraminidase (4.5 mUnits/well) was added in 150 mM NaCl, 50 mM sodium acetate, pH 5.5 and 0.1% CaCl$_2$ for 1 hour at 37° C. Wells were then blocked with binding buffer containing 10% FCS and tested for antibody binding by indirect ELISA.

TABLE 8

Effects of Neuraminidase Treatment on Antibody-Binding

| | | ABSORBANCE[1] | |
|---|---|---|---|
| Antibody | Mucin | Untreated | Treated |
| CONTROL | | | |
| C6 | H3300 | 5 | 440 |
| SENSITIVE | | | |
| W1 | H3300 | 1071 | 226 |
| W9 | H3300 | 412 | 2 |
| M26 | H3300 | 568 | 0 |
| INCREASED | | | |
| M8 | H3300 | 43 | 569 |
| M16 | H3300 | 472 | 751 |
| M25 | H3300 | 57 | 249 |
| M21 | W5-6 | 129 | 246 |
| M27 | MILK-2 | 232 | 598 |
| M29 | W5-6 | 176 | 276 |
| RESISTANT | | | |
| M10 | MCF7 | 756 | 837 |
| M11 | MCF7 | 515 | 584 |
| M12 | MCF7 | 1178 | 1188 |
| M15 | MILK-2 | 962 | 1278 |
| M22 | MILK-2 | 1282 | 1315 |
| M23 | MILK-2 | 1192 | 1282 |
| M38 | H3300 | 1228 | 1146 |

[1]Absorbance at 490 nm × 1000

Binding of the control antibody (C6) was increased by treatment, in accordance with the known preference of binding of this antibody to non-sialylated structures. Binding of antibodies M8, M16, M25, M21, M27 and M29 to H3300-derived mucin was also increased by neuraminidase treatment, suggesting that epitopes for these antibodies were unmasked by removal of sialic acid. In contrast, binding of these same antibodies to milk-derived mucins was unaffected by neuraminidase treatment.

Binding of antibodies W1 and W9 was neuraminidase sensitive, as has been demonstrated previously. Binding of antibody M26 was also neuraminidase sensitive, suggesting that sialic acid is required for binding of this antibody. Binding of the remaining seven antibodies was unaffected by neuraminidase treatment.

Since epitopes for most of the antibodies were not periodate or neuraminidase sensitive, it was possible that some of them would recognize core protein epitopes. To test this possibility, binding of certain antibodies to purified milk-derived mucin which had been deglycosylated by treatment with anhydrous hydrogen fluoride (HF) was studied. Milk-derived mucin was purified to homogeneity by affinity chromatography and size exclusion chromatography as described above was performed. Two hundred pg of purified protein (as determined by amino acid composition) was deglycosylated using anhydrous HF as described by Mort and Lamport, in *Anal. Biochem.* 82:289–309(1977), incorporated by reference herein. After treatment for four hours at 23° C., the sample was solubilized in 50% acetic acid, dialyzed against 20 mM ammonium acetate and lyophilized. Samples of untreated (3 ng protein/well) and deglycosylated (10 ng/well) were absorbed directly to polystyrene microtest wells, and tested for antibody binding by indirect ELISA.

To confirm that treatment had removed oligosaccharides, samples were subjected to amino acid and hexosamine analysis (AA Laboratories, Seattle, Wash.). Although the amino acid compositions of both samples were identical, the HF-treated mucin had a hexosamine (glucosamine+galactosamine) content of less than 2% that of untreated mucin. This treatment resulted in removal of more than 98% of N-acetyl glucosamine and N-acetyl galactosamine from the purified preparation, but did not significantly affect its amino acid composition.

TABLE 9

Binding of Antibodies to Deglycosylated Milk-Derived Mucin

| Antibody | ABSORBANCE[1] | |
|---|---|---|
| | Untreated | Treated |
| CONTROL | | |
| C6 | 819 | 5 |
| SENSITIVE | | |
| W1 | 1756 | 0 |
| W9 | 1101 | 0 |
| M8 | 2013 | 35 |
| M16 | 1703 | 8 |
| M25 | 934 | 15 |
| M38 | 2380 | 13 |
| RESISTANT | | |
| M15 | 1556 | 1525 |
| M22 | 1655 | 384 |
| M23 | 1609 | 2005 |
| M27 | 316 | 547 |

[1]Absorbance at 490 nm × 1000

As shown in Table 9, deglycosylation abolished binding of the control antibody, and six of ten antibodies which bound strongly to untreated mucin. In contrast, antibodies M15, M23 and M27 bound strongly to immobilized deglycosylated mucin, suggesting that these antibodies bind to epitopes on the core protein. Binding of antibody M22 was reduced by HF treatment, but binding was still significant. Antibodies M10, M11, M12, M21 and M29 were not tested for binding to core protein epitopes because these antibodies bound poorly to milk-derived mucin (Table 4).

As seen in this experiment, several antibodies (M15, M22, M23 and M27) bound to epitopes resistant to treatment with HF, which removed most of the carbohydrate from the protein core. Epitopes for these antibodies thus are most likely protein in nature.

The above tests reveal that relationships between epitopes recognized by the antibodies of this invention based on cross-competition analyses should be viewed in light of other treatments such as periodate, neuraminidase and deglycosylation. Thus, antibodies W9 and M8 show similar patterns of cross-competition (Table 6) but their epitopes can be distinguished on the basis of their sensitivities to periodate and neuraminidase treatments (Tables 7 and 8).

EXAMPLE VII

Serum Assay Using Monoclonal Antibodies M23, M26, M29 and M38

A DDIA was performed using the monoclonal antibodies Onc-M29 and Onc-M38, and Onc-M26 and Onc-M38 obtained as described in Example II. A homologous assay with Onc-M23 was also performed. Commercial test CA 15-3 (Centocor, Malvern, Pa.) and a homologous assay with W1 antibody were used for comparison. The assays were performed using a panel of sera comprising 72 samples from patients with metastatic breast cancer (M) and 94 samples from patients with benign breast disease (B) analyzed for antigen levels detected by DDIA as described in Example IV, except that antibody Onc-M29 was used as the capture antibody with Onc-M38 as the detecting antibody (M29/M38 "DDIA") and Onc-M26 was used as the capture antibody with Onc-M38 as the detecting antibody (M26/M38 "DDIA"). The results of these assays were compared to those from the homologous W1 assay and with the CA15-3 test in the experiment depicted in FIG. 5. The assays were compared in terms of their ability to discriminate between the two groups of patients with cutoff values chosen to give approximately 90% specificity (i.e., 90% of the control group tested negative).

Figure 5:
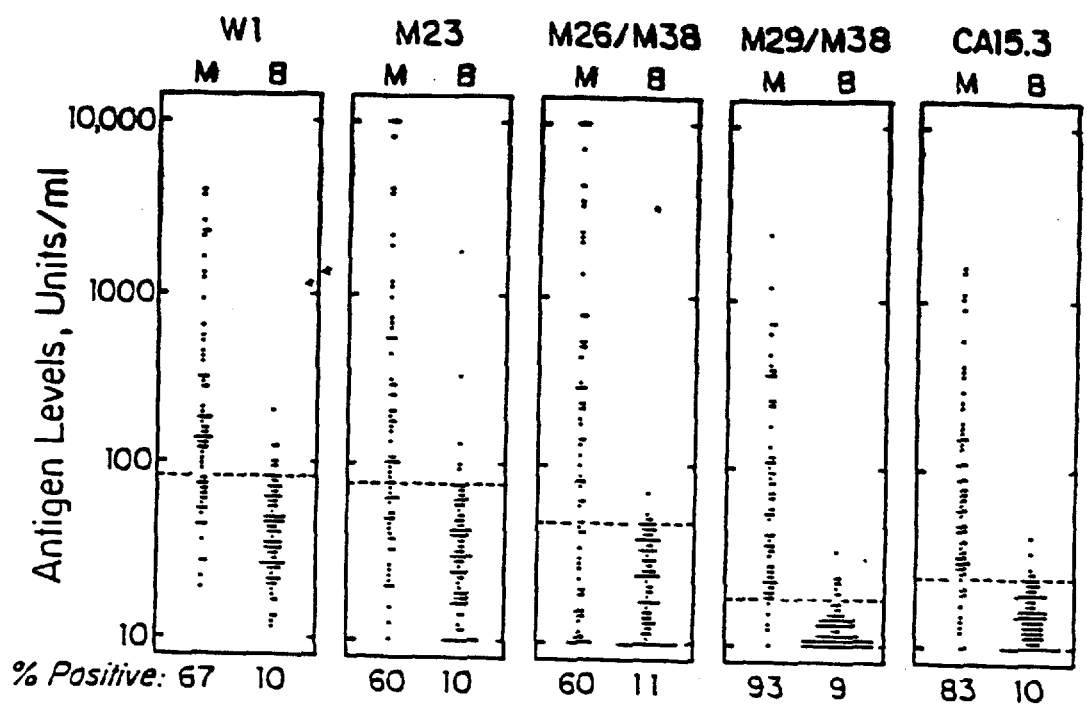
FIG. 5 is graphs showing levels of mucin antigen epitopes detected by DDIA in serum assays from breast cancer patients and patients with benign breast disease using monoclonal antibodies of this invention.

In FIG. 5, the values obtained are plotted such that the median of the control group for each test was positioned at approximately the 10th division on a linear scale having a total of 100 divisions. The dotted lines indicate values giving 90% specificity for each test. N is the number of samples tested.

This analysis showed that the assay with the best performance with this panel of sera was the M29/M38 heterologous assay, which detected 93% of metastatic breast cancer patients (gave 93% sensitivity). In comparison, the W1, M23, M26/M38 and CA 15.3 assays detected 67%, 60%, 60% and 83% of metastatic breast cancer patients, respectively. thus, different tests gave different results, with the M29/M38 and CA 15.3 tests showing better performance than the homologous W1 assay, and the M23 and M26/M38 assays showing equal or poorer performance.

Of the five tumor patient sera which tested negative with the M29/M38 test, two samples tested positive with the W1, M23, CA 15.3 tests, and one of these samples tested positive for the M26/M38 test. Thus, by combining M29/M38 results with an additional test 69/72 (95%) of tumor patient sera tested positive.

Tests were also evaluated for their ability to confirm results obtained with the M29/M38 assay. A number of tumor patients had serum antigen levels equal to or above the cut-off used in FIG. 5, but within the control range of values. Interpretation of these determinations is therefore subject to uncertainty because of the overlap with values determined for control samples. Improved detection of these patients would thus increase the clinical utility of the M29/M38 assay.

The most promising assay for this purpose was the M26/M38 assay (Table 10). A total of 24 of 72 sera from breast cancer patients gave M29/M38 values which were positive but below the highest value determined for control samples (≦35 units/ml). Of these 24 samples, 8 gave M26/M38 values which were outside the normal range (≧79 units/ml). Three of these samples gave M26/M38 levels which were more than three times the highest value detected for the control group. In contrast, 0/24, 0/24 and 3/24 serum samples had levels outside the normal range for the W1, M23 and CA 15.3 assays; in all cases the elevations for the latter assay were less than two-fold. Thus, while the M26/M38 assay detects fewer positives than the other tests, the levels obtained are sufficiently high that this test can be used to positively identify cancer patients who do not show strongly elevated values with other tests.

TABLE 10

Epitope Levels Detected by Different Tests In Sera from Patients with Metastatic Breast Carcinoma
TEST LEVELS (Units/ml)

| TEST SERUM | M29/M38 | W1 | M23 | M26/M38 | CA15-3 |
|---|---|---|---|---|---|
| 1 | 18 | 152 | 203 | 2140 | 61 |
| 2 | 19 | 121 | 86 | 1360 | 62 |
| 3 | 19 | 45 | 21 | 142 | 21 |
| 4 | 20 | 71 | 108 | 298 | 31 |
| 5 | 22 | 54 | 39 | 81 | 30 |
| 6 | 23 | 67 | 56 | 86 | 22 |
| 7 | 29 | 113 | 67 | 88 | 38 |
| 8 | 33 | 73 | 73 | 97 | 50 |

EXAMPLE VIII

Specificity of the Onc-M38 Antibody

To further demonstrate the specificity of the Onc-M38 monoclonal antibody of the present invention, imunohistology tests were performed using cancer and normal human tissues as described by Hellstrom et al., *Cancer Research* 46; pp. 3917–3923 (1986); incorporated by reference herein.

Carcinomas of the breast, lung (non-small cell lung cinomas (NSCLC)) and colon, and samples of various normal tissues were obtained at surgery from (Swedish Hospital Medical Center; the Virginia Mason Hospital, and Harborview Hospital in Seattle, Wash.) either as biopsies removed at surgery or in the form of pleural effusions.

Immediately upon removal from patients, tumor and normal tissue samples were frozen in liquid nitrogen, after which they were stored at −70° C. or in liquid $N^2$ until used.

Frozen sections were prepared, approximately 5 μm to 6 μm thick, and air dried for a minimum of 2 h. After treatment with acetone at −20° C. for 10 min, they were dried quickly with an air jet. Sections to be used for immunohistological staining were preincubated for 30 min with normal human serum diluted 1:5 in PBS. Parallel frozen sections were prepared and stained with hematoxylin:eosin for histological evaluation. For one set of experiments paraffin sections were prepared from tissues which had been fixed in Carnoy's solution immediately upon removal from the patients, embedded in paraffin, and sectioned; these sections were stained similarity to the frozen sections.

Immunohistological staining was performed using the PAP technique of Sternberger (In Immunocytochemistry, pp. 104–169, New York, John Wiley & Sons (1979)), as modified by Garrigues et al., *Int. J. Cancer*, 29, pp. 511–515 (1982) and Hellstrom et al., *J. Immunol.*, 130, pp. 1467–1472 (1983)), all of which are incorporated by reference herein. Onc-M38, rabbit anti-mouse immunoglobulin, and mouse PAP (Sternberger Meyer Cytoimmunochemicals, Inc., Jarrettsville, Md.) were diluted in a solution of 10% normal mouse serum and 3% rabbit serum in PBS. The staining procedure consisted of the following steps; (a) treatment for 1 h of sections with either specific or control antibody supernatant (e.g., myeloma protein (p117) diluted 1:2 in the serum mixture above); (b) application of rabbit anti-mouse immunoglobulin diluted 1:30; and (c) exposure to mouse PAP complex diluted 1:80. All antisera were incubated with the sections for 30 min at room temperature. Following antibody treatment, the slides were rinsed lightly with a stream of PBS and then washed twice in PBS.

The immunochemical reaction was developed by adding freshly prepared 0.05%, 3,3'-diaminobenzidine tetrahydrochloride and 0.01% hydrogen peroxide in 0.05M Tris buffer, pH 7.6, for 8 min. Further exposure to a 1% $OsO_4$ solution for 15 min intensified the reaction product. The sections were rinsed briefly with water, passed through increasing concentrations of alcohol, followed by xylene, and mounted with coverslips.

All slides were read by the same investigator who did not know their source. The degree of staining of tumor (or normal) cells was quantitated from "+" (very weak) to "4+" (very strong). A staining of "2+" or more was considered as "positive" and a staining of + or less as "negative."

Table 11 summarizes the immunohistology data using tumors and normal tissues. As shown in the table, Onc-M38 bound to at least 50% of the tumor tissue samples studied (with an intensity of at least 2+) but did not bind to any of the normal tissues.

TABLE 11

Immunohistology on Frozen Tissue Sections

| | ANTIBODY BINDING[1/] |
|---|---|
| CANCER TISSUES | |
| BREAST CANCER | 6/11 |
| LUNG CANCER | 2/4 |
| COLON CANCER | 3/3 |
| NORMAL TISSUES | |
| SPLEEN | 0/3 |
| KIDNEY | 0/7 |
| LIVER | 0/4 |
| LYMPHOCYTE PELLET | 0/3 |
| SKIN | 0/3 |
| BRAIN | 0/3 |
| COLON | 0/1 |
| BREAST | 0/1 |
| THYROID | 0/1 |

[1/]Antibody binding to tissue type indicated as number of positive (2+ or more) tumors/total number of tumors tested.

The data shown in Table 11 demonstrates that Onc-M38 recognizes relatively tumor-specific cell surface antigens on various carcinomas. Since selective localization of monoclonal antibody to tumor is required for therapy, the ability of Onc-M38 to bind to more than one tumor tissue type suggests the usefulness of this antibody for tumor therapy, alone or with other monoclonal antibodies of the present invention.

EXAMPLE IX

Assay to Detect Maliqnant Lung Disease Using Monoclonal Antibodies M26, M29 and M38

The ability of the mucin monoclonal antibodies of the present invention to detect mucin epitopes associated with diseased lung tissue was demonstrated by using bronchoscopy specimens and sera obtained from human subjects as follows.

Bronchial brushings were obtained during bronchoscopic examination of 27 subjects with lung-related complaints by Dr. Steve Springmeyer, Virginia Mason Hospital, Seattle, Wash. over a six-month period in 1987. Brushings were taken from the left and right lung of each patient according to standard bronchoscopy procedures and were analyzed using standard histological procedures. The results of the bronchoscopic examination and the histology tests together with additional information including chest X-rays, and CT scans, were used to separate the subjects into three groups: 17 benign (not proven to have malignant lung disease) individuals, 7 individuals with non small cell lung carcinoma (NSCLC), and three patients with other cancers (SCLC, prostate carcinoma and colon carcinoma). This last group will not be discussed further.

A DDIA was performed for comparison with the histological results using the monoclonal antibodies Onc-M29 and Onc-M38 and Onc-M26 and Onc-M38 to detect mucin antigen levels as described in Examples II and VII. Each bronchoscopy brushing specimen was placed in 0.5 ml of PBS saline and stored frozen at −70° C. until use. The specimen was then thawed at room temperature and microfuged for 10 minutes at 4° C. Each specimen was then diluted in a ratio of 1:11 (50 µl specimen and 500 µl sample diluent). In addition to bronchial specimens, the DDIA was also run on blood serum taken from each subject.

The epitope levels detected by the DDIA are presented in Table 12 for bronchial brushings and sera from the subjects indicated as benign and having NSCLC on the basis of the bronchoscopic examination and histology tests.

TABLE 12

Epitope Levels Detected by DDIA in Bronchial Specimens and Sera from Normal Subjects and Those Suspected of Lung Disease

| Subject | Diagnosis | Involved Lung | M26/M38 DDIA (units/ml) | | | M29/M38 DDIA (units/ml) | | |
|---|---|---|---|---|---|---|---|---|
| | | | L | R | S[1] | L | R | S |
| 1 | Benign | | 16 | 20 | 32 | 2 | 1 | 20 |
| 2 | Benign | | 17 | 32 | 3 | 2 | 3 | 11 |
| 3 | Benign | | 23 | 9 | 14 | 1 | 0 | 43 |
| 4 | Benign | | 43 | 55 | 16 | 0 | 1 | 15 |
| 5 | Benign | | 35 | 33 | 17 | 3 | 2 | 16 |
| 6 | Benign | | 57 | 49 | 24 | 2 | 1 | 19 |
| 7 | Benign | | 40 | 47 | 0 | 1 | 2 | 19 |
| 8 | Benign | | 100 | 100 | 18 | 2 | 2 | 9 |
| 9 | Benign | | 35 | 39 | 20 | 0 | 0 | 13 |
| 10 | Benign | | 17 | 18 | 11 | 1 | 1 | 8 |
| 11 | Benign | | 4 | 54 | 17 | 0 | 0 | 13 |
| 12 | Benign | | 43 | 27 | 23 | 2 | 1 | 22 |
| 13 | Benign | | 51 | 65 | 0 | 1 | 1 | 11 |
| 14 | Benign Carcinoid[2] | | 8 | 16 | 13 | 0 | 0 | 10 |
| 15 | Benign | | 24 | 23 | 0 | 0 | 0 | 42 |
| 16 | Benign | | 77 | 27 | 19 | 6 | 1 | 24 |
| 17 | Benign | | 25 | 46 | 29 | 1 | 1 | 12 |
| 18 | NSCLC (R) | | 13 | 29 | 15 | 0 | 3 | 11 |
| 19 | NSCLC (L) Liver Met[3] | | 720 | 72 | 610 | 24 | 2 | 104 |
| 20 | NSCLC (L) | | 347 | 51 | 1754 | 12 | 1 | 115 |
| 21 | NSCLC (R) | | 192 | 142 | 96 | 1 | 1 | 14 |
| 22 | NSCLC (L) | | 706 | 130 | 5 | 7 | 1 | 19 |
| 23 | NSCLC (R) | | 8 | 7 | 17 | 0 | 0 | 13 |
| 24 | NSCLC (L) | | 12 | 13 | 1 | 2 | 1 | 64 |

[1]Abbreviations: L = left lung; R = right lung and S = serum.
[2]Indicates benign tumor of bronchus
[3]Metastases As can be seen from Table 12, for the 17 individuals not proven by histological examination to have malignancy the M26/M38 DDIA on bronchial brushings from both lungs indicated epitope levels of 100 units/ml or less. The M29/M38 DDIA showed 6 units/ml or less. For the seven individuals diagnosed with NSCLC, the M26–M38 DDIA detected four patients having significantly elevated levels of epitope in the involved lung; the M29–M38 DDIA indicating three subjects with lung malignancy having elevated epitope levels in the involved lung. In two patients (Nos. 21 and 22) the M26/M38 levels in the uninvolved lung were elevated.

These results suggest that a significant percentage of patients undergoing early diagnostic procedures for suspected lung cancer had elevated levels of the mucin epitope markers detected by the antibodies of the present invention. Assay using these antibodies may thus prove useful for early detection of lung carcinoma and other carcinomas metastatic to the lungs that may escape detection by histological procedures.

With respect to results for sera, for benign subjects epitope levels were 54 units/ml or less in the M26/M38 DDIA and 43 units/ml or less in the M29/M38 DDIA. For the seven individuals diagnosed with NSCLC, the M26/M38 DDIA showed elevated antigen levels in three subjects and the M29/M38 assay also showed elevated antigen levels for three subjects. Thus, a relatively high proportion of subjects with lung cancer had high levels of these antigens in their sera, suggesting that the antibodies of this invention may be useful for early detection of lung cancer using such serum assays.

In addition to detecting mucin epitopes associated with lung cancer in bronchial brushings, other specimens may be tested with assays using the monoclonal antibodies of the invention and other antibodies against mucin epitopes. For example, bronchial lavage specimens and expectorated sputum may be diluted and similarly tested in an assay.

The new epitopes identified herein may serve as tumor markers for detecting tumors in patients. In addition, the new epitopes on the purified tumor-associated mucin antigens described herein and immunologically reactive with the new monoclonal antibodies may promote the development of more sensitive monoclonal antibodies for improved immunoassays. In particular, the monoclonal antibodies raised against tumor-associated mucin antigen using purified mucin (Onc-M8, Onc-M26, Onc-M29, Onc-M30 and Onc-M38) may prove useful in the early detection of cancer and for the implementation of cancer treatments. The Onc-M26 and Onc-M38 antibodies appear to show greater specificity for epitopes on mucin antigen derived from tumor sources than mucin antigen derived from normal sources. Tumor-associated mucin antigen may be detected in blood serum samples or other body fluids such as sputum, pleural effusion and milk, using immunoassays employing the monoclonal antibody Onc-M26 or M38 alone or in combination with any of the other monoclonal antibodies described herein, with additional monoclonal antibodies developed using purified mucin antigen as the immunogen, as well as with previously known antibodies such as W1 or W9 antibodies. The antibodies of this invention may be used in histological procedures to detect the presence of tumor-associated mucin antigen on cells from a mammal as well as to detect mucin present in fluid samples such as serum. By repeating these histological procedures over time, the progress of cancer in a patient may be monitored. For example, the antibodies described herein may be tested for binding to breast epithelium cells obtained from a patient to detect the presence of tumor-associated mucin antigen indicating that cancer cells may be present.

The Onc-M26 monoclonal antibody, as well as the other new antibodies described herein, may be assembled alone, or two or more of the antibodies may be used in combination, in diagnostic test kits with suitable instructions, for assaying the presence of tumor-associated mucin antigens in serum or other biological specimens. For example, a kit for performing a DDIA using Onc-M26 and Onc-M29 antibodies may contain a solid support, for example a microwell plate holder (Nunc, Newbury Park, Calif.) with sealers, containing one by eight strips with multiple wells. The strips have monoclonal antibody coated onto each well. Also included in the kit are assay reagents such as standards containing human antigen, for example, antigen from breast cancer pleural effusion, diluted in a suitable solution. The standards may consist of varying concentrations of antigen, for example, for ONC-M29 a first standard may consist of 4 units of M29 antigen/ml and a second standard of 10 units/ml. For ONC-M26 a first standard may consist of 30 units of M26 antigen/ml and a second standard of 75 units/ml. Controls are provided and may consist of the human antigen diluted in normal human serum (10% solution of M26 antigen and 11% solution of M29 antigen) with the antimicrobial agents.

In some cases, if a sample contains antigen at levels higher than 825 units/ml for M26 and 110 units/ml for M29 (higher than the highest standard) in an initial assay run, the specimen may be further diluted with an appropriate amount of the sample diluent. Dilutions may be made as follows:
1:11—50 µl test sample+500 µl sample diluent
1:55—50 µl 1:11 dilution+200 µl sample diluent
1:275—50 µl 1 1:55 dilution+200 µl sample diluent Conjugated antibody is also included in the kit. For example, antibody conjugated with the enzyme HRP is supplied in a separate container containing suitable diluent. Enzyme substrate, for example if the enzyme label is HRP, citrate buffered hydrogen peroxide and 3,3'5,5'-Tetramethylbenzidine in Dimethyl Sulfoxide (TMB chromogen), is included in a separate container in the kit for use in detecting the bound, conjugated antibody. Sample diluent and a reaction terminating reagent such as 1N sulfuric acid may be additional components of the kit. A wash solution (e.g. 10×PBS) may also be provided. The wash solution and terminating reagent are stored at room temperature. All other reagents are preferably kept at 4° C., but are brought to room temperature for use. It is preferable that standards and controls be run in duplicate.

For immunotherapy, any antibody selected from those described herein may be coupled to a radionuclide or other detectable label and introduced into the body of a mammal to image cancer cells or to conduct radiotherapy. Thus, the antibody chosen may be coupled to a radionuclide or antitumor drug and introduced into a mammal using any suitable method of introduction, including intravenous injection, to deliver the radionuclide or drug to tumor tissues containing antigen reactive with the antibody. The detectable label may be selected from among fluorophores, enzymes, chromophores, coenzymes, chemiluminescent materials, enzyme inhibitors, paramagnetic metals such as gadolinium, and radionuclides that are known in the art.

While the present invention has been described in conjunction with preferred embodiments, one of ordinary skill, after reading the foregoing specification, will be able to effect various changes, substitutions of equivalents, and alterations to the compositions and methods set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A hybridoma cell producing monoclonal antibody characterized by immunological binding to a mucin antigen, said antibody having an antigen combining site which competitively inhibits the immunospecific binding of an antibody selected from the group consisting of ATCC Numbers: HB 9248; HB 9212; HB 9210; HB 9243; and HB 9365 to its target antigen.

2. A monoclonal antibody produced by any one of the hybridoma cell lines of claim 1.

3. The monoclonal antibody of claim 2 coupled to a detectable label selected from the group consisting of enzymes, chromophores, fluorophores, coenzymes, chemiluminescent materials, enzyme inhibitors, paramagnetic materials, and radionuclides.

* * * * *

UNITED STATES PATENT AND TRADEMARK OFFICE
CERTIFICATE OF CORRECTION

PATENT NO. : 5,849,876
DATED : December 15, 1998
INVENTOR(S) : Linsley et al.

It is certified that error appears in the above-identified patent and that said Letters Patent is hereby corrected as shown below:

Column 13, line 29, "microtiters" should read —microtiter—

Column 13, line 37, "chromatoqraphy" should read —chromatography—

Column 27, lines 35 & 36, "imunohistology" should read —immunohistology—

Column 27, lines 39 & 40, "cinomas" should read —carcinomas—

Column 27, line 60, "similarity" should read —similarily—

Column 28, line 64, "Maliqnant" should read —Malignant—

Column 31, line 31, "50ul 1 1:55" should read —50ul 1:55—

Signed and Sealed this

Sixteenth Day of May, 2000

Attest:

Q. TODD DICKINSON

*Attesting Officer*      *Director of Patents and Trademarks*